(12) United States Patent
Jascomb et al.

(10) Patent No.: US 11,528,954 B2
(45) Date of Patent: *Dec. 20, 2022

(54) PERSONAL PROTECTION AND VENTILATION SYSTEM

(71) Applicant: O&M Halyard, Inc., Mechanicsville, VA (US)

(72) Inventors: Jerald T. Jascomb, Roswell, GA (US); Brian E. Lin, Cumming, GA (US); Dennis Joseph, Milton, GA (US); Prasad S. Potnis, Johns Creek, GA (US); Brian M. Collins, Johns Creek, GA (US); Namita A. Mithani, Alpharetta, GA (US)

(73) Assignee: O&M Halyard, Inc., Mechanicsville, VA (US)

(*) Notice: Subject to any disclaimer, the term of this patent is extended or adjusted under 35 U.S.C. 154(b) by 333 days.

This patent is subject to a terminal disclaimer.

(21) Appl. No.: 16/549,295

(22) Filed: Aug. 23, 2019

(65) Prior Publication Data
US 2020/0060375 A1    Feb. 27, 2020

Related U.S. Application Data

(60) Provisional application No. 62/722,571, filed on Aug. 24, 2018.

(51) Int. Cl.
*A42B 3/28* (2006.01)
*A42B 3/04* (2006.01)
(Continued)

(52) U.S. Cl.
CPC .......... *A42B 3/281* (2013.01); *A41D 13/1218* (2013.01); *A42B 3/044* (2013.01);
(Continued)

(58) Field of Classification Search
CPC .... A41D 13/1218; A42B 3/281; A42B 3/044; A42B 3/286
See application file for complete search history.

(56) References Cited

U.S. PATENT DOCUMENTS

| | | |
|---|---|---|
| 3,259,913 A | 7/1966 | Tames |
| 3,338,992 A | 8/1967 | Kinney |
| | (Continued) | |

FOREIGN PATENT DOCUMENTS

| | | |
|---|---|---|
| CN | 1242786 A | 1/2000 |
| CN | 102504422 A | 6/2012 |
| | (Continued) | |

OTHER PUBLICATIONS

Kimberly-Clark Corporation, "Aero Blue", 510K Summary, May 8, 2014, 9 pages.
(Continued)

*Primary Examiner* — Peter Y Choi
(74) *Attorney, Agent, or Firm* — Dority & Manning, P.A.

(57) ABSTRACT

A personal protection and ventilation system is provided. The system includes a gown having front and rear panels, a hood, and visor; a fan; an air tube; and a helmet. The fan is positioned between the wearer and a body-facing surface of the rear panel. The front panel and at least a portion of the hood are formed from a first material including a first spunbond layer, a spunbond-meltblown-spunbond laminate, and a liquid impervious elastic film disposed therebetween. The first material has an air volumetric flow rate of less than about 1 standard cubic feet per minute (scfm). The rear panel is formed from a second material including a nonwoven laminate having an air volumetric flow rate of about 20 scfm to about 80 scfm. Therefore, the fan is able to intake a sufficient amount of air from the environment through the rear panel to provide cooling/ventilation to the hood.

20 Claims, 18 Drawing Sheets

(51) Int. Cl.

| | | |
|---|---|---|
| *B32B 27/32* | (2006.01) | |
| *B32B 5/26* | (2006.01) | |
| *B32B 27/12* | (2006.01) | |
| *A41D 13/12* | (2006.01) | |
| *A61B 90/00* | (2016.01) | |
| *A62B 18/00* | (2006.01) | |
| *A62B 17/00* | (2006.01) | |
| *A62B 18/04* | (2006.01) | |
| *A62B 9/00* | (2006.01) | |
| *A62B 17/04* | (2006.01) | |

(52) U.S. Cl.
 CPC ............. *A42B 3/286* (2013.01); *A61B 90/05* (2016.02); *A62B 9/006* (2013.01); *A62B 17/006* (2013.01); *A62B 17/04* (2013.01); *A62B 18/003* (2013.01); *A62B 18/045* (2013.01); *B32B 5/269* (2021.05); *B32B 27/12* (2013.01); *B32B 27/327* (2013.01); *B32B 2262/0253* (2013.01); *B32B 2437/00* (2013.01); *B32B 2571/00* (2013.01)

(56) References Cited

U.S. PATENT DOCUMENTS

| | | |
|---|---|---|
| 3,341,394 A | 9/1967 | Kinney |
| 3,359,569 A | 12/1967 | Rotanz et al. |
| 3,502,763 A | 3/1970 | Hartmann |
| 3,542,615 A | 11/1970 | Dobo et al. |
| 3,692,618 A | 9/1972 | Dorschner et al. |
| 3,696,443 A | 10/1972 | Taylor |
| 3,754,284 A | 8/1973 | Hartigan et al. |
| 3,790,964 A | 2/1974 | Hartigan |
| 3,802,817 A | 4/1974 | Matsuki et al. |
| 3,849,241 A | 11/1974 | Butin et al. |
| 3,864,757 A | 2/1975 | Hartigan |
| 3,868,728 A | 3/1975 | Krzewinski |
| 3,921,221 A | 11/1975 | Zoephel |
| 3,935,596 A | 2/1976 | Allen, Jr. et al. |
| 4,017,909 A | 4/1977 | Brandriff |
| 4,041,203 A | 8/1977 | Brock et al. |
| 4,054,952 A | 10/1977 | Swallow |
| 4,106,120 A | 8/1978 | Zurbrigg et al. |
| 4,340,563 A | 7/1982 | Appel et al. |
| 4,395,782 A | 8/1983 | Reynolds |
| 4,408,357 A | 10/1983 | Toth |
| 4,535,481 A | 8/1985 | Ruth-Larson et al. |
| 4,558,468 A | 12/1985 | Landry et al. |
| 4,674,132 A | 6/1987 | Stein et al. |
| 4,823,404 A | 4/1989 | Morell et al. |
| 4,843,641 A | 7/1989 | Cusick et al. |
| 4,845,779 A | 7/1989 | Wheeler et al. |
| 4,901,716 A * | 2/1990 | Stackhouse ........ A41D 13/1153 128/201.25 |
| 4,937,299 A | 6/1990 | Ewen et al. |
| 4,978,719 A | 12/1990 | Wong |
| 4,978,721 A | 12/1990 | Wong |
| 4,988,770 A | 1/1991 | Wong |
| 5,005,216 A | 4/1991 | Blackburn et al. |
| 5,015,695 A | 5/1991 | Wong |
| 5,027,438 A | 7/1991 | Scbwarze et al. |
| 5,145,727 A | 9/1992 | Potts et al. |
| 5,169,706 A | 12/1992 | Collier, IV et al. |
| 5,178,931 A | 1/1993 | Perkins et al. |
| 5,188,885 A | 2/1993 | Timmons et al. |
| 5,218,071 A | 6/1993 | Tsutsui et al. |
| 5,272,236 A | 12/1993 | Lai et al. |
| 5,278,272 A | 1/1994 | Lai et al. |
| 5,322,728 A | 6/1994 | Davey et al. |
| 5,331,683 A | 7/1994 | Stone et al. |
| 5,386,595 A | 2/1995 | Kuen et al. |
| 5,403,302 A | 4/1995 | Roessler et al. |
| 5,430,620 A * | 7/1995 | Li ............................ F21L 14/00 362/105 |
| 5,447,792 A | 9/1995 | Brandt et al. |
| 5,461,724 A | 10/1995 | Wiedner et al. |
| 5,472,775 A | 12/1995 | Obijeski et al. |
| 5,539,056 A | 7/1996 | Yang et al. |
| 5,571,619 A | 11/1996 | McAlpin et al. |
| 5,596,052 A | 1/1997 | Resconi et al. |
| 5,657,752 A * | 8/1997 | Landis .................. A61M 16/06 128/201.28 |
| 5,813,052 A | 9/1998 | Taylor |
| 5,932,497 A | 8/1999 | Morman et al. |
| 5,991,921 A | 11/1999 | Saito |
| 5,997,981 A | 12/1999 | McCormack et al. |
| 6,015,764 A | 1/2000 | McCormack et al. |
| 6,049,907 A | 4/2000 | Palomo |
| 6,090,325 A | 7/2000 | Wheat et al. |
| 6,111,163 A | 8/2000 | McCormack et al. |
| 6,332,221 B1 | 12/2001 | Gracey |
| 6,460,187 B1 | 10/2002 | Siegel |
| 6,461,457 B1 | 10/2002 | Taylor et al. |
| 6,481,019 B2 | 11/2002 | Diaz et al. |
| 6,500,563 B1 | 12/2002 | Datta et al. |
| 6,622,311 B2 | 9/2003 | Diaz et al. |
| 6,851,125 B2 | 2/2005 | Fujikawa et al. |
| 6,954,946 B2 | 10/2005 | Goldfarb et al. |
| 6,973,677 B2 | 12/2005 | Diaz et al. |
| 7,048,818 B2 | 5/2006 | Krantz et al. |
| 7,285,595 B2 * | 10/2007 | Quincy, III ............... B32B 5/26 428/421 |
| D565,279 S | 4/2008 | Farrell |
| 7,424,750 B2 | 9/2008 | Kerr |
| 7,491,196 B2 | 2/2009 | Franke et al. |
| 7,549,179 B1 | 6/2009 | Saied |
| 7,725,992 B2 | 6/2010 | Efremova et al. |
| 7,752,682 B2 | 7/2010 | VanDerWoude et al. |
| 7,785,309 B2 | 8/2010 | Van Gompel et al. |
| 7,802,313 B2 | 9/2010 | Czajka |
| 7,937,775 B2 * | 5/2011 | Manzella, Jr. ..... A41D 13/0025 2/410 |
| D646,463 S | 10/2011 | Petrovskis et al. |
| 8,101,534 B2 | 1/2012 | Dharmarajan et al. |
| 8,206,366 B2 | 6/2012 | Datta et al. |
| 8,234,722 B2 | 8/2012 | VanDerWoude et al. |
| 8,282,234 B2 | 10/2012 | VanDerWoude et al. |
| 8,332,965 B1 | 12/2012 | Ryer |
| 8,407,818 B2 | 4/2013 | VanDerWoude et al. |
| 8,721,827 B2 | 5/2014 | Chang et al. |
| 8,726,414 B2 | 5/2014 | Baron et al. |
| 8,819,869 B2 | 9/2014 | VanDerWoude et al. |
| 8,990,966 B2 | 3/2015 | Von Furstenberg et al. |
| D741,569 S | 10/2015 | Fredrickson |
| 9,173,437 B2 | 11/2015 | VanDerWoude et al. |
| 9,224,508 B2 | 12/2015 | Reynolds |
| 9,706,808 B2 | 7/2017 | Sclafani et al. |
| 10,201,207 B2 | 2/2019 | VanDerWoude et al. |
| 10,271,916 B2 | 4/2019 | Allen |
| 10,384,084 B2 | 8/2019 | Isham et al. |
| 10,420,386 B1 | 9/2019 | Jefferis et al. |
| 10,449,397 B2 | 10/2019 | VanDerWoude et al. |
| 2002/0142692 A1 | 10/2002 | Ferencz |
| 2003/0126668 A1 | 7/2003 | Scroggins |
| 2003/0157859 A1 | 8/2003 | Ishikawa |
| 2003/0192537 A1 * | 10/2003 | Odell ..................... A62B 31/00 128/201.25 |
| 2004/0006815 A1 | 1/2004 | Carroll et al. |
| 2005/0079372 A1 | 4/2005 | Schmal et al. |
| 2005/0132463 A1 | 6/2005 | Kathumbi-Jackson et al. |
| 2005/0132465 A1 | 6/2005 | Kathumbi-Jackson et al. |
| 2006/0096003 A1 | 5/2006 | Plaatje et al. |
| 2006/0160453 A1 | 7/2006 | Suh |
| 2006/0172647 A1 * | 8/2006 | Mehta ...................... D04H 3/16 442/327 |
| 2006/0251858 A1 | 11/2006 | Thomas et al. |
| 2008/0268190 A1 | 10/2008 | Shi et al. |
| 2009/0068912 A1 | 3/2009 | Boscolo et al. |
| 2009/0165186 A1 | 7/2009 | Mijares et al. |
| 2009/0286906 A1 | 11/2009 | Shi et al. |
| 2010/0108067 A1 * | 5/2010 | Walker ................. A62B 18/006 128/205.24 |
| 2011/0003524 A1 | 1/2011 | Claasen et al. |

(56) References Cited

U.S. PATENT DOCUMENTS

| | | |
|---|---|---|
| 2011/0024485 A1 | 2/2011 | Porowski |
| 2012/0045956 A1 | 2/2012 | Tau et al. |
| 2012/0054940 A1 | 3/2012 | Halseth |
| 2012/0167287 A1 | 7/2012 | Mould-Millman |
| 2012/0233737 A1 | 9/2012 | Slot |
| 2012/0285464 A1 | 11/2012 | Birch et al. |
| 2012/0329354 A1 | 12/2012 | Afshari |
| 2012/0330258 A1 | 12/2012 | Poruthoor |
| 2013/0086775 A1 | 4/2013 | Raymond |
| 2013/0305426 A1 | 11/2013 | Walrich et al. |
| 2013/0318693 A1 | 12/2013 | McBride et al. |
| 2014/0082823 A1 | 3/2014 | Gordon et al. |
| 2014/0127461 A1 | 5/2014 | Xu et al. |
| 2014/0189931 A1 | 7/2014 | Fredrickson |
| 2015/0059390 A1 | 3/2015 | Hayes |
| 2015/0150316 A1 | 6/2015 | Champagne et al. |
| 2015/0150318 A1 | 6/2015 | Terrell |
| 2015/0210038 A1 | 7/2015 | Ichikawa et al. |
| 2015/0233031 A1 | 8/2015 | Kunimoto et al. |
| 2018/0084848 A1 | 3/2018 | Pavalarajan et al. |
| 2018/0125127 A1* | 5/2018 | Harris ................ B32B 5/024 |
| 2018/0263326 A1 | 9/2018 | Ulmer et al. |
| 2019/0150534 A1 | 5/2019 | Jascomb |
| 2019/0174860 A1 | 6/2019 | VanDerWoude et al. |
| 2019/0231005 A1 | 8/2019 | Jefferis et al. |
| 2019/0344101 A1 | 11/2019 | Isham et al. |
| 2020/0001123 A1 | 1/2020 | VanDerWoude et al. |

FOREIGN PATENT DOCUMENTS

| | | |
|---|---|---|
| CN | 203789203 U | 8/2014 |
| DE | 29703238 U1 | 4/1997 |
| DE | 202007012469 U1 | 3/2008 |
| EP | 1 228 712 B1 | 9/2005 |
| EP | 2 8532169 A1 | 4/2015 |
| GB | 1 492 553 | 11/1977 |
| JP | 2007092258 A | 4/2007 |
| KR | 20050001019 A | 1/2005 |
| KR | 101475151 B1 | 12/2014 |
| KR | 101483363 B1 | 1/2015 |
| WO | WO 95/02973 | 2/1995 |
| WO | WO 99/06207 A1 | 2/1999 |
| WO | WO 03/049937 A1 | 6/2003 |
| WO | WO 2005/066406 A1 | 7/2005 |
| WO | WO 2005/120263 A1 | 12/2005 |
| WO | WO 2007/008168 A1 | 1/2007 |
| WO | WO 2007/140163 A2 | 12/2007 |
| WO | WO 2014/071897 A1 | 5/2014 |
| WO | WO 2014/199273 A1 | 12/2014 |
| WO | WO 2014/199278 A1 | 12/2014 |
| WO | WO 2015/075632 A1 | 5/2015 |
| WO | WO 2017/192654 A1 | 11/2017 |

OTHER PUBLICATIONS

Kleenguard, http://www.medline.com/product/KLEENGUARD-A40-Breathable-Back-Coveralls-by-Kimberly-Clark/Z05-PF98272, no date given, 2 pages.

Micromax, http://www.lakeland.com/media/wysiwyg/Diposables/mm_ns_cs_2_11_2015, no date given, 1 page.

TyvekDual, http://www.safespec.dupont.co.uk/safespec/en/product/1060.html?refNm=Recent, 2017, 5 pages.

Mölnlycke Health Care, "Surgical Gown Materials", http://www.molnlycke.com.au/Documents/AUS-NZL/Surgical/Gown_MaterialSheet_PS0511_050_V1_Aus, no date given, 2 pages.

Dymex Healthcare, "Isolation Gown", http://www.dymexhealthcare.com/Products/Isolation-Gown/142907012054469.html, no date given, 2 pages.

Dymex Healthcare, "Coverall", http://dymexhealthcare.com/Products/Coverall/143149496469203.html, no date given, 2 pages.

Encompas, "Personal Protective Equipment Catalog", http://www.encompassgroup.net/content/pdf/Encompass_PPE_Catalog, 2011, 28 pages.

Amaryllis Healthcare, "Surgical Gowns", http://www.amaryllishealthcare.in/surgical-gowns.html, no date given, 3 pages.

Jingzhou Haixin Green Cross Medical Products Catalog, online, http://hh-greencross.en.alibaba.com, no date given.

Medline Textiles, "Medline Catalog", https://cdn.shopify.com/s/files/1/0380/0221/files/Medline_Textile_Patient_Apparel.pdf, no date given, 32 pages.

Tidi Products "Tidi Products Catalog", http://www.tidiproducts.com/wp-content/uploads/2014/12/Medical-Catalog-Winter-2014.pdf, no date given, 48 pages.

Chang et al., "Electro-Optical Light Management Material: Low Refractive Index Pressure Sensitive Adhesives", no date given, 14 pages.

A.P. Kharitonov, "Practical applications of the direct fluorination of polymers", Journal of Fluorine Chemistry, vol. 103, Russia, 2000, pp. 123-127.

International Search Report and Written Opinion for PCT/IB2019/057126, dated Nov. 19, 2019, 12 pages.

* cited by examiner

PERSONAL PROTECTION AND VENTILATION SYSTEM

RELATED APPLICATION

This application claims priority to U.S. Provisional Application No. 62/722,571 entitled "Personal Protection and Ventilation System," filed on Aug. 24, 2018, the contents of which are incorporated herein by reference.

FIELD OF THE INVENTION

The present invention relates to protective garments such as surgical gowns, hoods, helmets, and ventilation systems worn by medical care providers in the operating room or people in any other environment where exposure to hazardous materials and liquids is a risk.

BACKGROUND OF THE INVENTION

Surgeons and other healthcare providers often wear a combination of a surgical suit or gown, a hood, and an air cooling or ventilation system during operating procedures, particularly orthopedic total joint replacement surgeries such as arthroplasties and revisions of the knee, hip, and shoulder, in order to ensure sterile conditions in the operating room, protect the wearer, and create a comfortable environment for the wearer in terms of ventilation and cooling. Such a total protection suit can include a surgical gown, a hood with a viewing visor, and a ventilation system that can include a fan and battery. However, the ventilation systems associated with currently available systems are noisy, causing communication problems and preventing the wearer from fully utilizing the cooling air capacity because as it is turned up to full capacity, the wearer is unable to hear others or communicate effectively with others in the operating room. Moreover, currently available systems utilize a non-disposable, heavy helmet structure where the fan and other components of the ventilation system are incorporated into the helmet structure, as the air intake for the fan is usually pulled in from the hood, which is formed from a breathable filtration-type material since the surgical gown itself is typically not breathable and is instead impervious to air due to the requirement that it be a barrier to fluids such as blood. Such a design where the fan is incorporated into the helmet structure can lead to head and neck strain and "bobble headedness" due to the top-heavy nature of helmets where the fan is incorporated into the helmet design. Moreover, because currently available systems are expensive to manufacture and are thus reused by hospital staff, the maintenance, cleaning, and tracking of the numerous pieces of equipment associated with such systems is expensive, time consuming, and requires the use of additional hospital resources.

Further, in order to prevent the spread of infection to and from the patient, the surgical gowns that are part of the aforementioned systems function to prevent bodily fluids and other liquids present during surgical procedures from flowing through the gown. Disposable surgical gowns are typically made entirely from fluid repellent or impervious fabrics to prevent liquid penetration or "strike through." Various materials and designs have been used in the manufacture of surgical gowns to prevent contamination in different operating room conditions. While gowns made from an impervious material do provide a high degree of protection, gowns constructed of this type of material are typically heavy, restrictive, expensive, and uncomfortably hot to the wearer. While efforts have been made to utilize a lighter weight material in order to provide for better breathability and help reduce the overall weight of the gown, the higher the breathability of the material, the lower the repellency of the material, where the material may not meet the minimum guidelines that have been created for the rating of the imperviousness of surgical gowns.

Specifically, the Association for the Advancement of Medical Instrumentation (AAMI) has proposed a uniform classification system for gowns and drapes based on their liquid barrier performance. These procedures were adopted by the American National Standards Institute (ANSI) and were recently published as ANSIA/AAMI PB70: 2012 entitled Liquid Barrier Performance and Classification of Protective Apparel and Drapes Intended for Use in Health Care Facilities, which was formally recognized by the U.S. Food and Drug Administration in October 2004. This standard established four levels of barrier protection for surgical gowns and drapes. The requirements for the design and construction of surgical gowns are based on the anticipated location and degree of liquid contact, given the expected conditions of use of the gowns. The highest level of imperviousness is AAMI level 4, used in "critical zones" where exposure to blood or other bodily fluids is most likely and voluminous. The AAMI standards define "critical zones" as the front of the gown (chest), including the tie cord/securing means attachment area, and the sleeves and sleeve seam area up to about 2 inches (5 cm) above the elbow.

As such, a need exists for an economical disposable personal protection and ventilation system that can be discarded after just a few uses or as little as a single use and that provides sufficient cooling to the wearer without causing head and neck strain. In addition, a need exists for a surgical garment (e.g., a surgical gown) that meets the AAMI level 4 standard while at the same time being stretchable, soft, breathable, and cool to maximize the comfort for the wearer (e.g., medical care providers).

SUMMARY OF THE INVENTION

In accordance with one embodiment of the present invention, a personal protection and ventilation system is provided. The personal protection and ventilation system includes a disposable surgical gown comprising a front panel, a first sleeve, a second sleeve, a first rear panel, a second rear panel, a hood, and a visor, wherein the front panel, the first sleeve, the second sleeve, and at least a part of the hood are formed from a first material comprising an outer spunbond layer having a surface that defines an outer-facing surface of the disposable surgical gown, a spunbond-meltblown-spunbond (SMS) laminate having a surface that defines a body-facing surface of the disposable surgical gown, and a liquid impervious elastic film disposed therebetween, wherein the elastic film meets the requirements of ASTM-1671, wherein the first material allows for an air volumetric flow rate of less than about 1 standard cubic feet per minute (scfm), and wherein the first rear panel and the second rear panel are formed from a second material comprising a nonwoven laminate that is air breathable, wherein the second material allows for an air volumetric flow rate ranging from about 20 scfm to about 80 scfm; a helmet having a first side and a second side, an air conduit extending from a rear portion of the helmet to a front portion of the helmet to define an air outlet, and a head band having a front portion and a rear portion, wherein the rear portion of the head band includes a cradle; a fan module comprising a fan, wherein the fan module is about a waist of the wearer, wherein the fan intakes air from an outside environment through the first rear panel of the disposable surgical gown, the second rear panel of the disposable surgical gown, or both; and an air tube, wherein the air tube delivers air taken in from the fan module to the helmet, wherein the cradle engages with the air tube, wherein the air conduit then delivers the air to the air outlet at the front portion of the helmet to provide ventilation to the wearer.

In one particular embodiment, the air outlet can be positioned at an angle α that ranges from about 5° to about 60° with respect to an x-axis or horizontal direction towards a y-axis or vertical direction.

In another embodiment, the air conduit and the head band can be formed from a polymer, cellulose, or a combination thereof.

In still another embodiment, the hood can be formed completely from the first material.

In yet another embodiment, a first portion of the hood can be formed from the first material and a second portion of the hood can be formed from the second material, wherein the first portion and the second portion can be separated by a seam located at a rear of the disposable surgical gown, wherein the first portion can be located above the seam and can include all of the hood above the seam, and wherein the second portion can be located below the seam.

In one more embodiment, the visor can include a first connecting tab present on a first side of the visor and a second connecting tab present on a second side of the visor, wherein the helmet can include a first receiving tab on the first side of the helmet and a second receiving tab present on the second side of the helmet, wherein the first and second connecting tabs and the first and second receiving tabs can secure the disposable surgical gown to the helmet when engaged.

In an additional embodiment, the head band can include padding disposed between the front portion of the head band and the wearer.

In another embodiment, the helmet can include a securing band extending between the first side of the helmet and the second side of the helmet, wherein the securing band can include an adjustment strap located on the first side of the helmet, the second side of the helmet, or both.

In still another embodiment, a light source can be attached to the front portion of helmet. Further, the light source can be contained within a support mounted to the first portion of the helmet, further wherein the support can include a lever to adjust an area of illumination of the light source.

In yet another embodiment, the elastic film can include a core layer disposed between a first skin layer and a second skin layer, wherein the core layer can include polypropylene and the first skin layer and the second skin layer can each include copolymer of polypropylene and polyethylene.

In one more embodiment, the elastic film can have a basis weight ranging from about 5 gsm to about 50 gsm.

In one particular embodiment, the core layer can include a fluorochemical additive present in an amount ranging from about 0.1 wt. % to about 5 wt. % based on the total weight of the core layer.

In an additional embodiment, the core layer can include a filler that is present in the core layer in an amount ranging from about 50 wt. % to about 85 wt. % based on the weight of the core layer.

In another embodiment, the outer spunbond layer and the SMS laminate can include a semi-crystalline polyolefin, wherein the semi-crystalline polyolefin can include a copolymer of propylene and ethylene, wherein the ethylene is present in an amount ranging from about 1 wt. % to about 20 wt. %.

In still another embodiment, the outer spunbond layer can have a basis weight ranging from about 5 gsm to about 50 gsm and the SMS laminate can have a basis weight ranging from about 10 gsm to about 60 gsm.

In yet another embodiment, the outer spunbond layer and the SMS laminate can each include a slip additive, wherein the slip additive can include erucamide, oleamide, stearamide, behenamide, oleyl palmitamide, stearyl erucamide, ethylene bis-oleamide, N,N'-Ethylene Bis(Stearamide) (EBS), or a combination thereof, wherein the slip additive can be present in the outer spunbond layer in an amount ranging from about 0.1 wt. % to about 4 wt. % based on the total weight of the outer spunbond layer, and wherein the slip additive can be present in a layer of the SMS laminate in an amount ranging from about 0.25 wt. % to about 6 wt. % based on the total weight of the layer.

In one more embodiment, the first rear panel and the second rear panel can each include a SMS laminate. Further, the first rear panel and the second rear panel can each have a basis weight ranging from 20 gsm to about 80 gsm.

In an additional embodiment, the first rear panel and the second rear panel can include a slip additive that can include erucamide, oleamide, stearamide, behenamide, oleyl palmitamide, stearyl erucamide, ethylene bis-oleamide, N,N'-Ethylene Bis(Stearamide) (EBS), or a combination thereof, wherein the slip additive can be present in the first rear panel and the second rear panel in an amount ranging from about 0.25 wt. % to about 6 wt. % based on the total weight of each spunbond layer in the SMS laminate of the first rear panel and the second rear panel.

In another embodiment, a sound level of about 15 decibels to about 45 decibels can be required for the wearer to hear 90% of words spoken by another person with the fan operating at a low speed, wherein a sound level of about 30 decibels to about 50 decibels can be required for the wearer to hear 90% of words spoken by another person with the fan operating at a high speed.

These and other features, aspects and advantages of the present invention will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE FIGURES

A full and enabling disclosure of the present invention to one skilled in the art, including the best mode thereof, is set forth more particularly in the remainder of the specification, including reference to the accompanying figures, in which.

Figure 1:
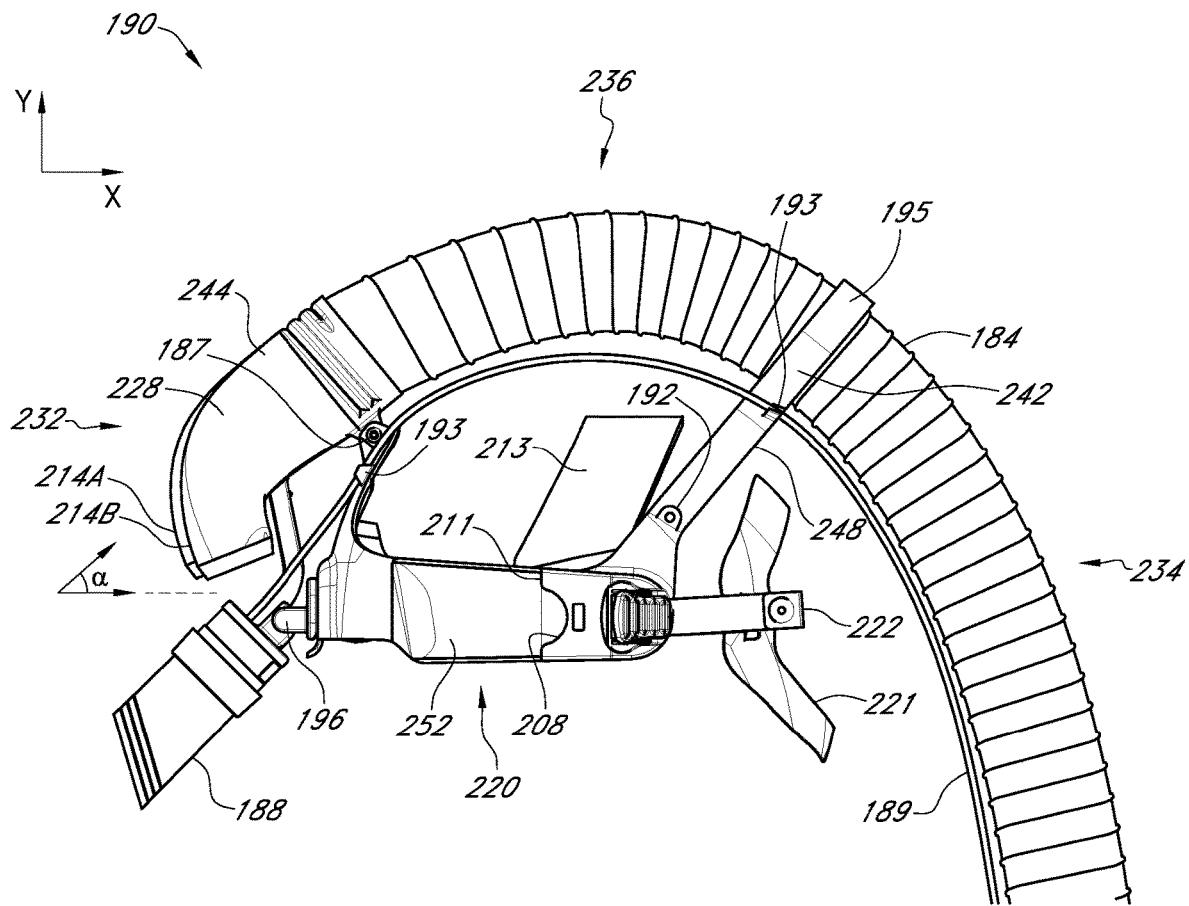
FIG. 1 illustrates a side view of a helmet that is part of the personal protection and ventilation system contemplated by the present invention.

Repeat use of reference characters in the present specification and drawings is intended to represent the same or analogous features or elements of the present invention.

DEFINITIONS

As used herein, the term "spunbond" refers to fabric made from small diameter fibers which are formed by extruding molten thermoplastic material as filaments from a plurality of fine, usually circular capillaries of a spinneret with the diameter of the extruded filaments then being rapidly reduced as by, for example, in U.S. Pat. No. 4,340,563 to Appel et al., and U.S. Pat. No. 3,692,618 to Dorschner et at, U.S. Pat. No. 3,802,817 to Matsuki et al., U.S. Pat. Nos. 3,338,992 and 3,341,394 to Kinney, U.S. Pat. No. 3,502,763 to Hartman, and U.S. Pat. No. 3,542,615 to Dobo et al. Spunbond fibers are generally not tacky when they are deposited onto a collecting surface. Spunbond fibers are generally continuous and have average diameters (from a sample of at least 10) larger than 7 microns, more particularly, between about 10 and 20 microns.

As used herein, the term "meltblown" refers to fabric formed by extruding a molten thermoplastic material through a plurality of fine, usually circular, die capillaries as molten threads or filaments into converging high velocity, usually hot, gas (e.g. air) streams which attenuate the filaments of molten thermoplastic material to reduce their diameter, which may be to microfiber diameter. The meltblown fibers are then carried by the high velocity gas stream and are deposited on a collecting surface to form a web of randomly dispersed meltblown fibers. Such a process is disclosed, for example, in U.S. Pat. No. 3,849,241 to Butin et al. Meltblown fibers are microfibers which may be continuous or discontinuous, are generally smaller than 10 microns in average diameter, and are generally tacky when deposited onto a collecting surface.

As used herein, the term "SMS laminate" refers to fabric laminates of spunbond and meltblown fabrics, e.g., spunbond/meltblown/spunbond laminates as disclosed in U.S. Pat. No. 4,041,203 to Brock et al., U.S. Pat. No. 5,169,706 to Collier et al, U.S. Pat. No. 5,145,727 to Potts et al., U.S. Pat. No. 5,178,931 to Perkins et al. and U.S. Pat. No. 5,188,885 to Timmons et al. Such a laminate may be made by sequentially depositing onto a moving forming belt first a spunbond fabric layer, then a meltblown fabric layer and last another spunbond layer and then bonding the laminate in a manner described below. Alternatively, the fabric layers may be made individually, collected in rolls, and combined in a separate bonding step. Such fabrics usually have a basis weight of from about 0.1 osy to 12 osy (about 3.4 gsm to about 406 gsm), or more particularly from about 0.75 to about 3 osy (about 25.4 gsm to about 101.7 gsm).

DETAILED DESCRIPTION OF REPRESENTATIVE EMBODIMENTS

Reference now will be made in detail to various embodiments of the invention, one or more examples of which are set forth below. Each example is provided by way of explanation of the invention, not limitation of the invention. In fact, it will be apparent to those skilled in the art that various modifications and variations may be made in the present invention without departing from the scope or spirit of the invention. For instance, features illustrated or described as part of one embodiment, may be used on another embodiment to yield a still further embodiment. Thus, it is intended that the present invention covers such modifications and variations as come within the scope of the appended claims and their equivalents.

Generally speaking, the present invention is directed to a personal protection and ventilation system. The system includes a disposable surgical gown comprising a front panel, a first sleeve, a second sleeve, a first rear panel, a second rear panel, a hood, and a visor. The front panel, the first sleeve, the second sleeve, and at least a part of the hood are formed from a first material that includes an outer spunbond layer having a surface that defines an outer-facing surface of the disposable surgical gown, a spunbond-meltblown-spunbond (SMS) laminate having a surface that defines a body-facing surface of the disposable surgical gown, and a liquid impervious elastic film disposed therebetween. Further, the elastic film meets the requirements of ASTM-1671, and the first material allows for an air volumetric flow rate of less than about 1 standard cubic feet per minute (scfm). Meanwhile, the first rear panel and the second rear panel are formed from a second material that includes a nonwoven laminate that is air breathable, where the second material allows for an air volumetric flow rate ranging from about 20 scfm to about 80 scfm.

The system also includes a helmet, and a fan component or module. The helmet includes an air conduit that extends from a rear portion of the helmet to a front portion of the helmet to define an air outlet that can be in the form of a bifurcated tube that includes two air outlets. The helmet also includes a head band, where the head band can be foldable or movable in order to provide support to the air conduit. For instance, the head band can include a front portion and a rear portion connected via a hinge, where the rear portion can include a cradle that engages with the air conduit in order to support the air tube, which can be somewhat flexible. Further, the head band can be foldable or movable at the hinge where the front portion and the rear portion meet to adjust the location along the air tube at which the cradle is positioned. Meanwhile, the fan component or module can be secured to a user's scrubs about the wearer's waist, such as via a clip. The fan component or module includes a fan, where the fan is positioned so as to intake air from an outside environment through the first rear panel, the second rear panel of the disposable surgical gown, or both. Further, the air tube delivers air taken in from the fan component or module to the helmet, wherein the air conduit then delivers the air to the air outlet at the front portion of the helmet to provide ventilation/cooling to the wearer.

As mentioned above, the front panel and at least a part of the hood are formed from a first material that includes a first spunbond layer, a nonwoven (e.g., SMS) laminate, and a liquid impervious elastic film disposed therebetween that provides little to no air permeability (e.g., the first material allows for an air volumetric flow rate of less than about 1 standard cubic feet per minute (scfm)). While wearing such a disposable surgical gown, the wearer or user can easily overheat and get hot to the point of discomfort and distraction. Therefore, a ventilation system of cooling air delivery is provided by use of a fan component or module that can include a fan and a power source (e.g., a battery) that delivers cooling air through an air tube to an air conduit in a helmet that distributes cooling to one or more air outlets to the wearer's face and head region inside the hood for comfort and prevention of visor fogging, which can impair vision during surgery.

Moreover, the helmet is designed to be ultra-lightweight and has a low-profile support structure that is very comfortable, yet is sufficiently rigid to support the hood and visor without discomfort. Further, the visor utilizes a pair of connecting tabs on each side that lock into or engage with receiving tabs on each side of the helmet to securely attach the hood to the helmet. Additionally, because hearing and poor communication are common problems with current personal protection and ventilation systems, the system of the present invention utilizes a waist-mounted fan that significantly reduces noise within the hood compared to systems that utilize helmet-mounted fans. In other words, because the fan is positioned near the waist of the wearer, the noise level to which the wearer is subjected inside the surgical gown and hood is reduced compared to currently available systems where the fan component or module is incorporated into the helmet and/or hood structure. For instance, during auditory testing of the personal protection and ventilation system of the present invention, a sound level of only about 15 decibels to about 45 decibels, was required for the wearer to hear 90% of words spoken by another person while the wearer was donning the personal protection and ventilation system of the present invention with the fan set at a low speed. In contrast, a sound level of about 50 decibels to about 70 decibels was required for the wearer to hear 90% of words spoken by another person while the wearer was donning a currently available personal protection and ventilation system with the fan set at a low speed. In addition, a sound level of only about 30 decibels to about 50 decibels was required for the wearer to hear 90% of words spoken by another person while the wearer was donning the personal protection and ventilation system of the present invention with the fan set at a high speed. In contrast, a sound level of about 60 decibels to about 95 decibels was required for the wearer to hear 90% of words spoken by another person while the wearer was donning a currently available personal protection and ventilation system with the fan set at a high speed. Thus, as shown from the auditory testing data above, communication during a surgical or other medical procedure is improved with the personal protection and ventilation system of the present invention.

Specifically, because of the arrangement of the fan component or module as a component that is separate from the helmet and hood and that is positioned near a waist of the wearer, cooling air is drawn into the surgical gown via the fan through the rear panel of the surgical gown of the present invention, which is sufficiently air breathable to draw in enough air to provide cooling to the system and is delivered through an air tube to the helmet where the cooling air is directed to the user's head and face. For instance, the rear panel can be formed from a nonwoven laminate that is air breathable yet still provides some level of moisture/liquid barrier protection and allows for an air volumetric flow rate ranging from about 20 standard cubic feet per minute (scfm) to about 80 scfm. Therefore, the fan is able to intake a sufficient amount of air from the environment through the rear panel in order to provide cooling and ventilation to the hood in that it functions as an air filter medium. In addition, the visor is wide-angled for maximum viewing ease and peripheral vision during a surgical procedure, which also aids in communication between surgical team members by exposing the face. This present invention can also include an optional accessory light for enhanced illumination of the surgical site opening (e.g., a joint site during an orthopedic procedure). Each of the components of the personal protection and ventilation system is discussed in more detail below, where the non-sterile components and sterile components are discussed separately.

I. Non-Sterile Components (Helmet, Air Tube, and Fan Module with Charging Unit)

Figure 2:
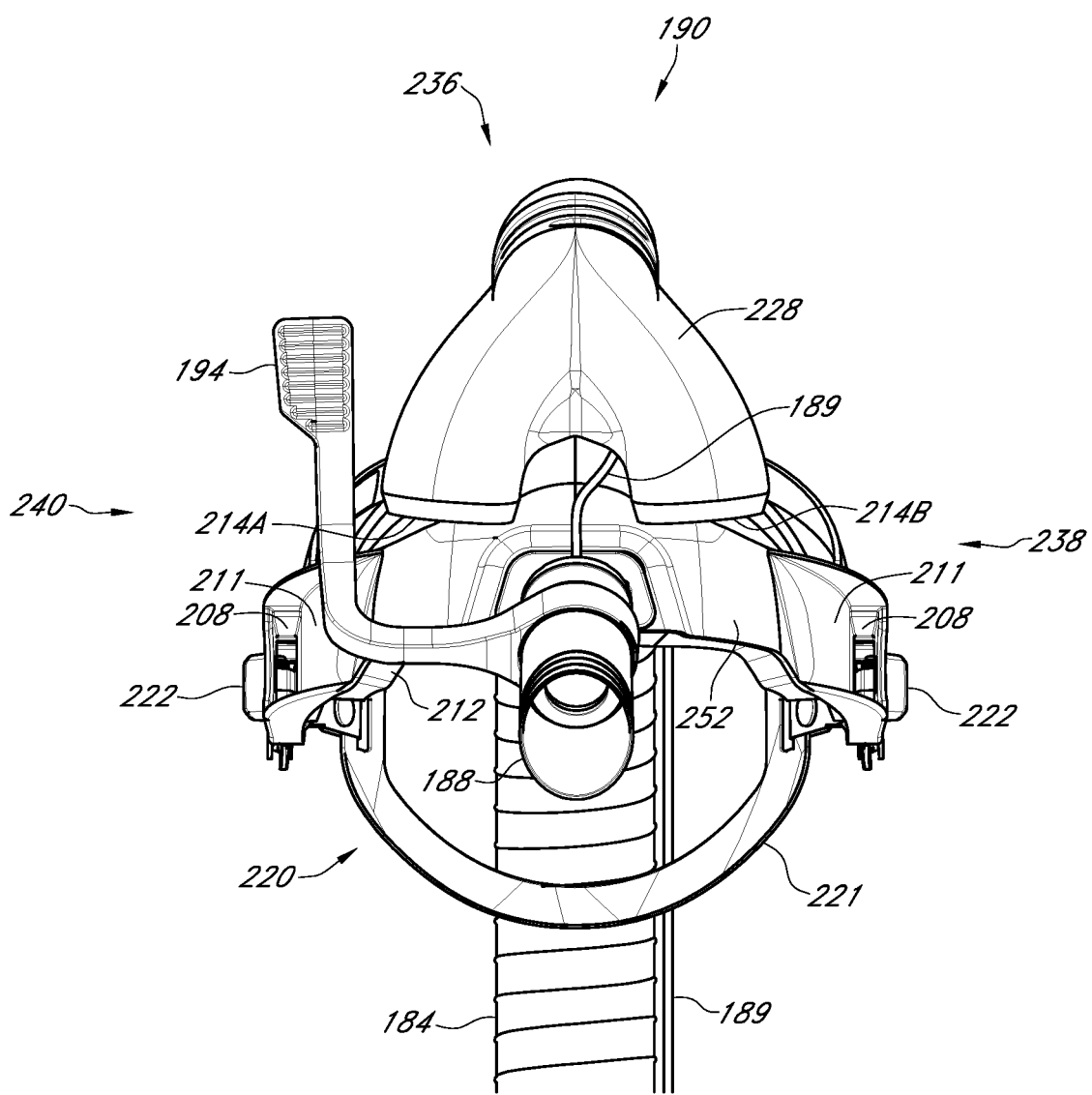
FIG. 2 illustrates a front view of the helmet of FIG. 1.

FIGS. 1-2 and 5-9 illustrate the various non-sterile components of the personal protection and ventilation system of the present invention, and specifically illustrate the helmet 190, air tube 184, and fan module 186, along with the fan module charging unit 270. Referring to FIGS. 1 and 2, the helmet 190, which has a front portion 232, rear portion 234, a first side 28, a second side 240, and a top portion 236, can include a head band 220, an air conduit 228, and an optional light source 188.

The head band 220 can include a front portion 252, a rear portion 248, and a top portion 213. The front portion 252 of the head band 220 extends from a first side 238 of the helmet to a second side 240 of the helmet. Further, the rear portion 248 of the head band 220 can be connected to the front portion 252 of the head band 220 at a hinge 192 present on either side of the helmet 190 at the front portion 252 of the head band 220. Meanwhile, the top portion 213 of the head band can be positioned between the front portion 252 of the head band 220 and the rear portion 248 of the head band 220.

Figure 3:
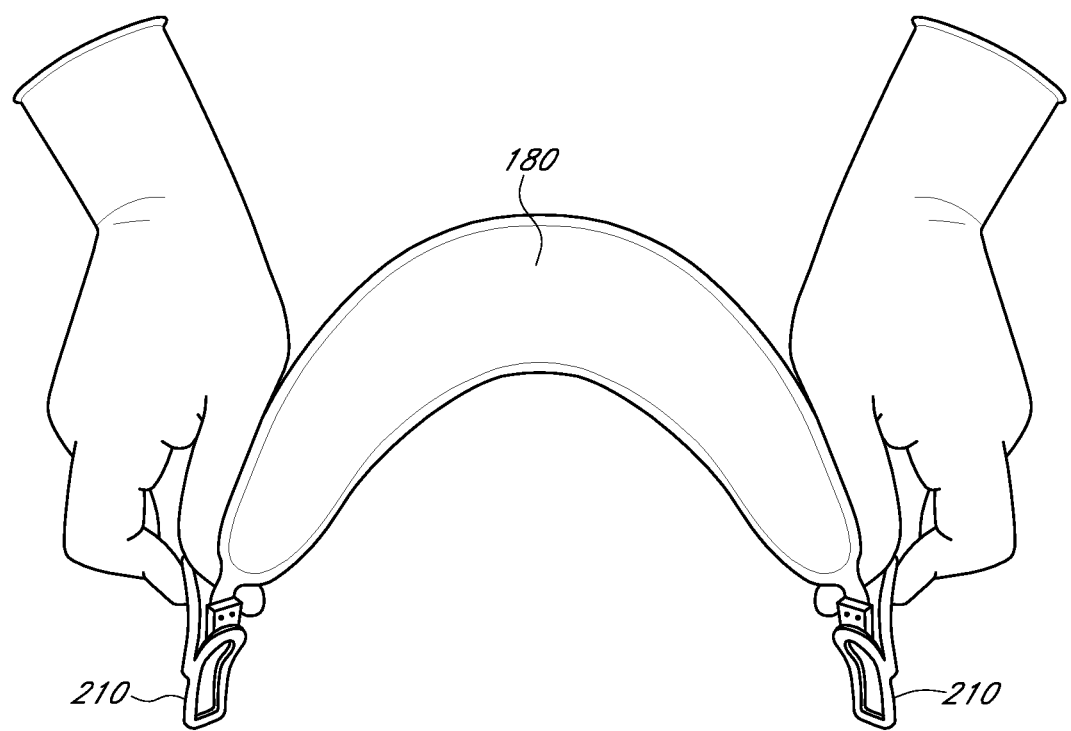
FIG. 3 illustrate a top view of a visor that may be used in conjunction with the helmet of FIGS. 1 and 2.
Figure 4:
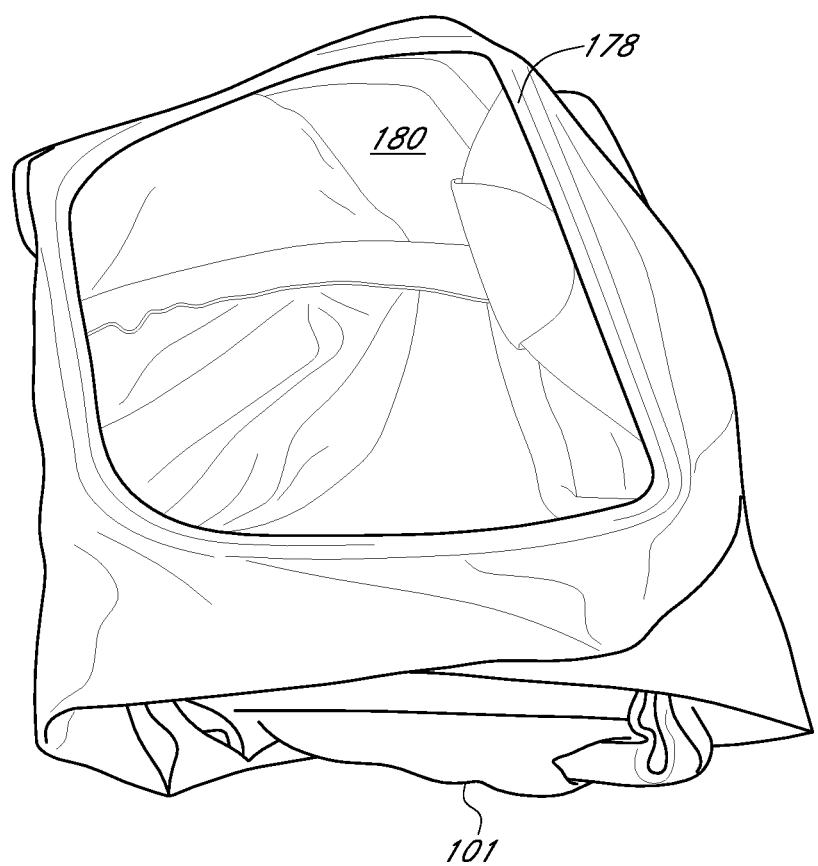
FIG. 4 illustrates a perspective view of a disposable surgical gown including a hood and a visor contemplated by the personal protection and ventilation system of the present invention.
Figure 5:
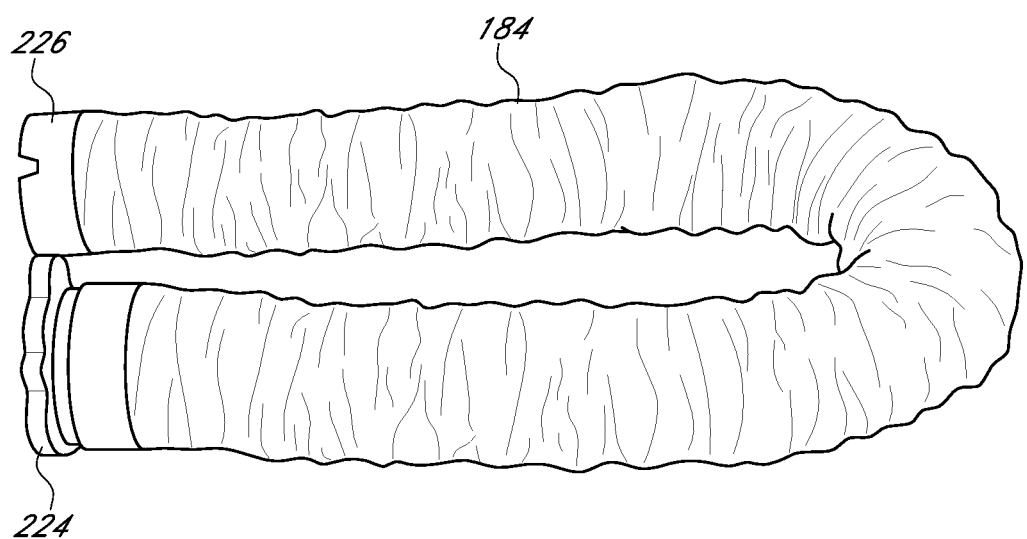
FIG. 5 illustrates an air tube contemplated by the personal protection and ventilation system of the present invention.

As shown in FIGS. 1-2, the front portion 252 of the head band 220 can include receiving tabs 208 and guide rails 211 for connecting with the hood 178 via connecting tabs 210 on the visor 178 portion of the hood 178 of the gown 101 (see FIGS. 3-4). In addition, the front portion 252 of the head band 220 can include a hinge or hinged connection point 187 for connecting the air conduit 228 to the head band 220 portion of the helmet 190, as well as a hinge or hinged connection point 196 for connecting the optional light source 188 to the head band 220.

The air conduit 228 includes an air outlet that can be in the form of two bifurcated air outlets 214A and 214B, although it is to be understood that in some embodiments, a single air outlet without bifurcations can be utilized. However, without intending to be limited by any particular theory, the present inventors have found that the bifurcated air tube outlets 214A and 214B help improve the distribution and circulation of air around the sensitive part of the face and around that head and neck region for maximum cooling without the additional noise that a single air outlet might produce. The air conduit 228 extends from the rear portion 234 to the front portion 234 along a top portion 236 of the helmet 190, where the air conduit 228 includes at least one hollow channel for supplying air from the air tube 184 to the front portion 232 of the helmet 190 at one or more air outlets 214. The air conduit 228 also includes an air tube connector 244 for connecting the air tube 184 to the helmet 190. As further shown in FIG. 1, the air outlets 214A and 214B can be positioned at an angle α that ranges from about 5° to about 60°, such as from about 10° to about 55°, such as from about 15° to about 40° with respect to a x-axis or horizontal direction towards a y-axis or vertical direction, as allowed by the hinged connection point 187. Without intending to be limited by any particular theory, it is believed that such angles falling within the aforementioned ranges allow for a direction of air flow that reduces fogging in the visor, limits drying of the wearer's eyes, and also provides sufficient cooling to the optional light source 188.

As shown in FIGS. 1-2, the optional light source 188 that can be attached to the helmet 190 at the hinge or hinged connection point 196 can be adjusted with a lever 194 so that the light from the light source 188 is directed in the desired area by a user. For instance, the lever 194 allows for adjusting the angle of the light source 188 so that the user can adjust the illumination area of the light source 188 based on his or her preference. The light source 188 can be formed from a metal or polymer, while the lever 194 and the support 196 can be formed from any suitable polymer, cellulose, or a combination thereof that provides sufficient rigidity while being lightweight at the same time. For example, the lever 194 and hinge or hinged-connection point 196 can be formed from a molded polymer, molded cellulose, a foamed polymer, a hollow polymer, etc. In addition, the light source 188 can be in the form of a light emitting diode (LED) light source and can include a silicone shroud to reduce glare that may be reflected by the visor 180. Further, the light source 188 can be powered via a battery 216 present within the fan module 186 and can be connected to the fan module 186 via a power cable 189. Further, the power cable 189 can be secured to the helmet 190 via receiving rails 193 to keep the power cable 189 from possibly interfering with the wearer's field of vision while wearing the helmet 190.

As mentioned above, the head band 220 can also include a rear portion 248 including a cradle 242 for receiving the air tube 184. As shown, the cradle 242 supports the air tube 184, which delivers air from the fan 182 in the fan module 186, where the position of the cradle 242 can be adjustable along the length of the air tube 184 because of the hinge 192 connecting the front portion 252 and rear portion 248 of the head band 220. Further, it is to be understood that the air tube 184 can be permanently attached to the cradle 242 via an adhesive, or it can be temporarily attached via a hook and loop wrap 195 as shown. Further, as shown in FIG. 1, the head band 220 can include a top portion 213 that can be in the form of a foam material to enhance the comfort of the head band 220.

In addition, it is to be understood that the air conduit 228 and head band 220 can be made from any suitable polymer, cellulose, or a combination thereof in order to further reduce the overall weight of the helmet 190 and minimize costs while being sufficiently rigid to support all of the components of the system 100. As such, the helmet 190 can be disposable or limited to single-day use while minimizing the costs to the hospital or other medical facility at the same time. For instance, the air conduit 228 and the head band 220 can be formed from a molded polymer, molded cellulose, a foamed polymer, a hollow polymer, etc., where the use of such materials results in a helmet having a much lower than the weight of the helmets used in currently available personal protection and ventilation systems.

Referring still to FIGS. 1-2, the helmet 190 can also include a securing means or band 221 extending between the first side 238 and the second side 240 of the helmet 190 at the crown of the wearer's head and at the back of the wearer's head that can be used to securely fit the helmet 190 to each individual wearer via adjustment means 222 (e.g., straps) that can be adjusted via pulling or loosening the adjustment means 222 on the first side 238 and the second side 240 of the helmet 190 at receiving tabs 208. In one embodiment, the adjustment means 222 can include toggle switches to effectively grip the pull straps for tightening and holding the straps to the position the user pulls the straps to for a secure and snug fit. In addition, the helmet 190 can include padding 212 at the front portion 232 of the helmet 190 adjacent the front portion 252 of the head band 220 in order to provide comfort to the user or wearer and to secure the helmet 190 as the adjustment means 222 are tightened or loosened as needed.

Figure 6:
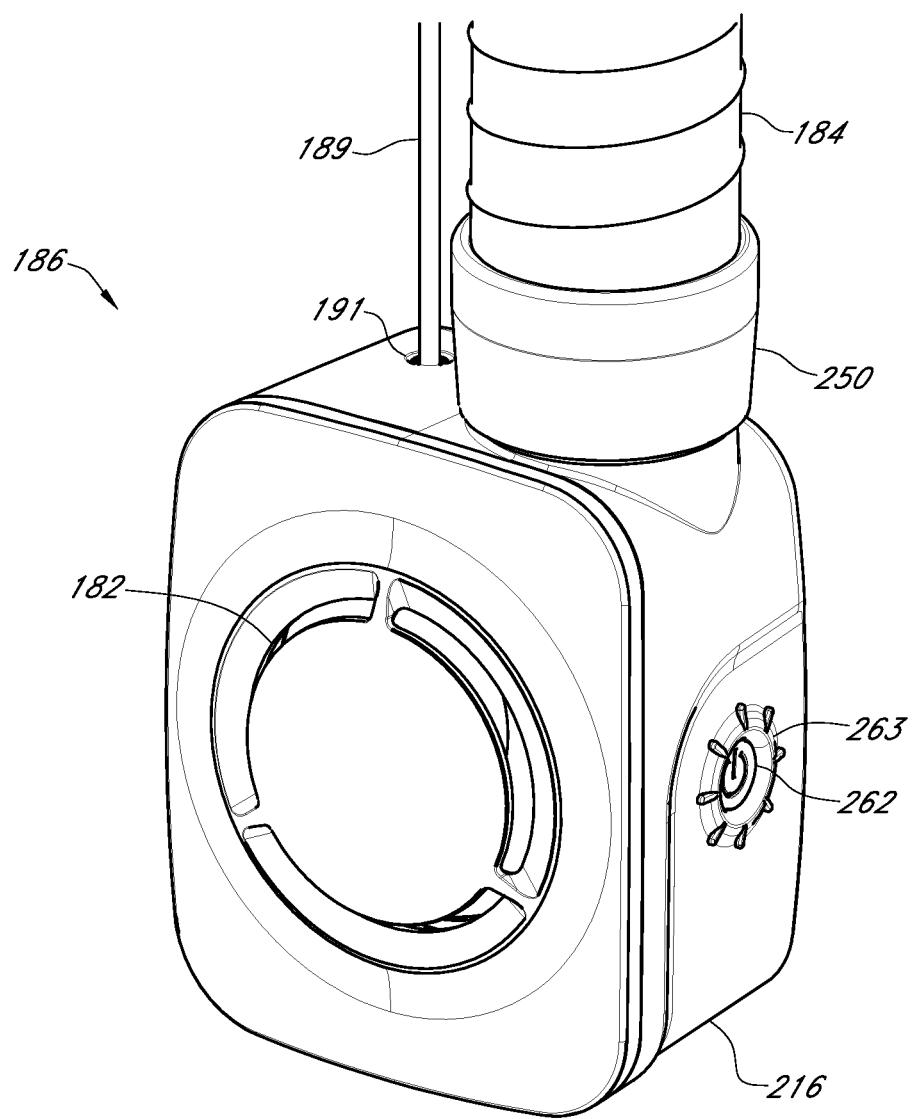
FIG. 6 illustrates a perspective view of a fan component or module connected to an air tube contemplated by the personal protection and ventilation system of the present invention.
Figure 7:
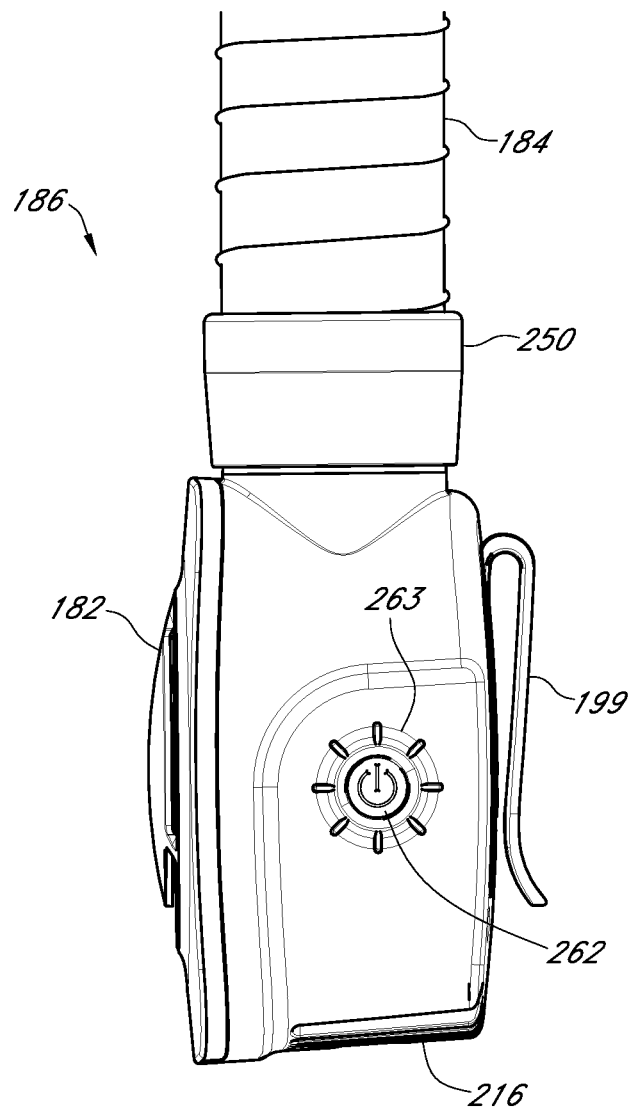
FIG. 7 illustrates a side view of a fan component or module connected to an air tube contemplated by the personal protection and ventilation system of the present invention.

As mentioned above and referring to FIG. 5, the personal protection and ventilation system also includes an air tube 184 having a fitting 226 at one end that attaches to the air tube connector 244 on the helmet 190 and a fitting 224 at the opposite end that attaches to the air tube connector 250 on the fan module 186 (see FIGS. 6-7). Further, the air tube 184 can be connected to the air tube connector 244 with an adhesive to ensure a secure connection.

Turning now to FIGS. 6-9, the fan component or module 186 includes a fan 182 and can also include a built-in power source 216 such as a battery, and a power and fan speed adjustment button 262 with, for example, low, medium, and high fan speed settings, that can be positioned within a recess 263 to as to avoid inadvertent pressing of the button. In one embodiment, the power source 216 can include one or more batteries that provide power to the fan 182. In addition, the power source 216 can include a low battery indicator that is provided in the form of a sound, vibration, or haptic feedback so that the user or wearer can be alerted as to when the power source 216, whether it be located within the fan component or module 186 (see FIG. 1) or included in the system 100 as a separate component, needs to be recharged or its batteries replaced. Further, it is also to be understood that the power source 216 can be a separate component from the fan component or module 186.

Figure 17A:
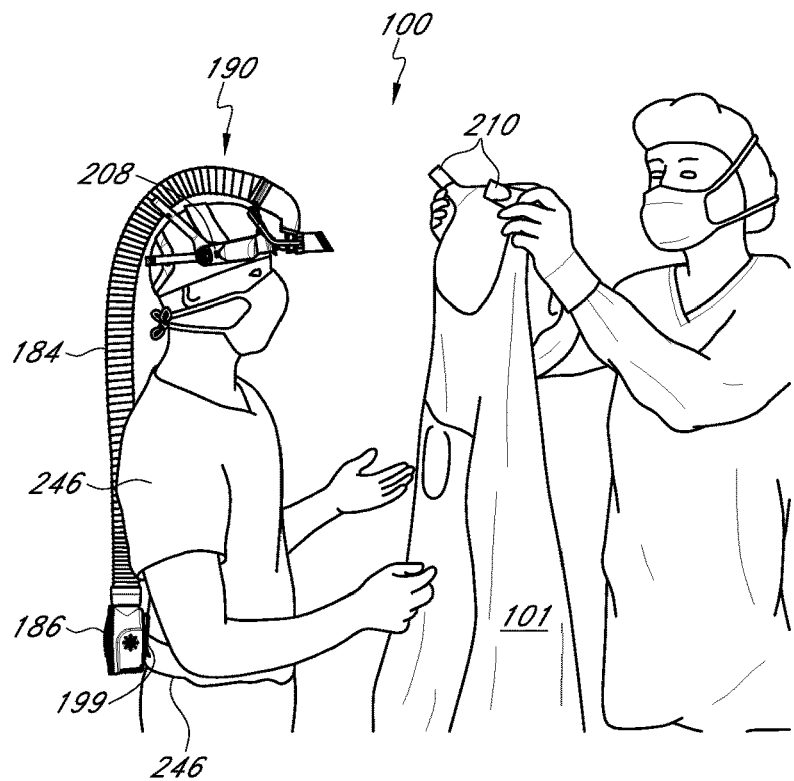
FIGS. 17A, 17B, 17C, 17D, 17E, and 17F illustrate a procedure for donning the disposable surgical gown and hood of a personal protection and ventilation system contemplated by the present invention.

In addition, the air tube 184 can be attached to the fan component or module 186 via fitting 224 at air tube connector 250 as mentioned above. Moreover, the fan component or module 186 can be attached about a wearer's waist (e.g., on the waistband of scrubs 246 as shown in FIG. 17A) such as via a clip 199 to secure the fan component or module 186 about the rear waist area of a wearer. FIG. 6 illustrates a perspective view of the fan component or module 186, while FIG. 7 illustrates a side view of a fan component or module 186 that can be attached to an article of clothing (e.g., scrubs) near a wearer's waist according to embodiment of the personal protection and ventilation system of the present invention. As mentioned above, the light source 188 can be powered via the battery 216 present within the fan module 186 and can be connected to the fan module 186 at power cable receptacle 191 via a power cable 189.

Figure 8:
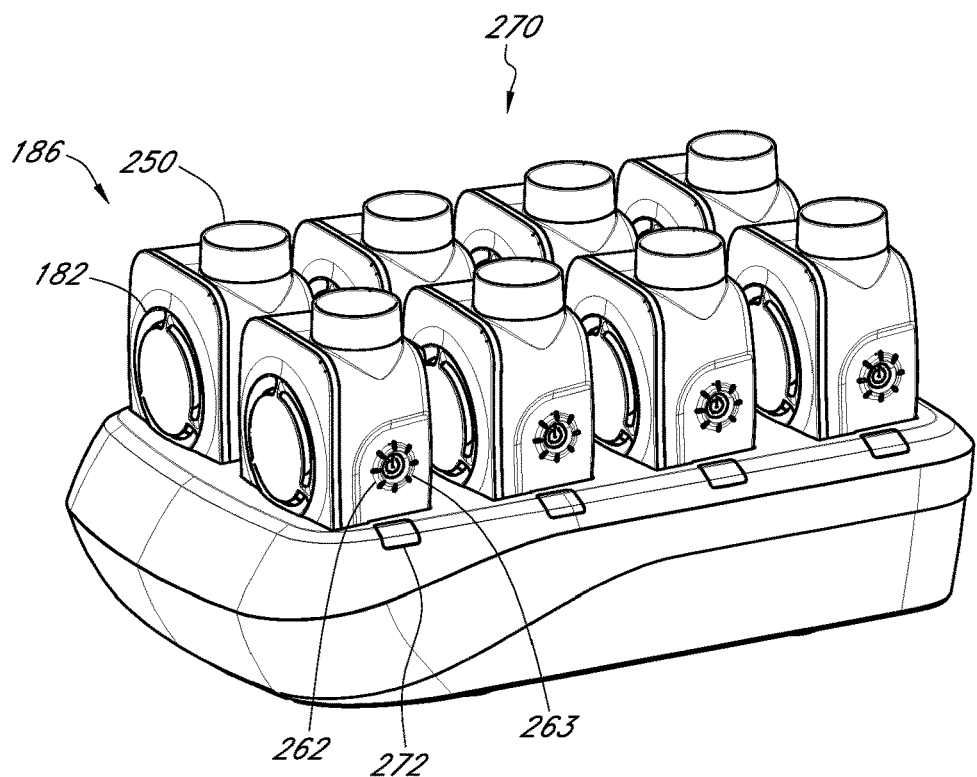
FIG. 8 illustrates a side perspective view of a charging unit for a plurality of fan components or modules contemplated by the personal protection and ventilation system of the present invention.
Figure 9:
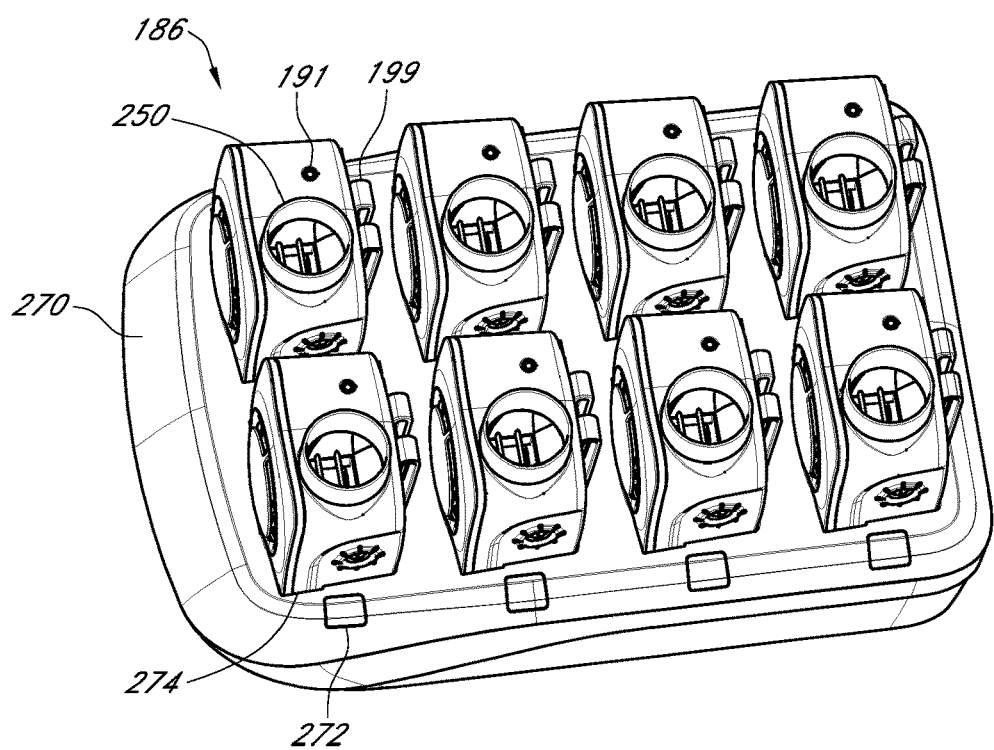
FIG. 9 illustrates a top perspective view of a charging unit for a plurality of fan components or modules contemplated by the personal protection and ventilation system of the present invention.

Moreover, as shown in FIGS. 8-9, the present invention can also include a fan module charging unit 270 that includes one or more recesses 274 to hold one or more fan modules 186 in order to recharge the power source 216 (e.g., battery). Further the fan module charging unit 270 can include an indicator light 272 associated with each recess 274 that can alert a user that the power source 216 is fully charged. For instance, the indicator light 272 can change from unlit to green or from red to green when the fan module 186 being charged in a particular recess 274 is fully charged and ready for use. Further, the indicator light 272 can be an amber or orange color when a fan module 186 is still charging.

FIG. 17A illustrates a side view of a user wearing the helmet 190, air tube 184, and fan component or module 186 contemplated by one embodiment of the personal protection and ventilation system of the present invention. As shown, the fan component or module 186 can be worn about the user or wearer's waist over scrubs 246 so that the fan component or module 186 is positioned at the user or wearer's back. Further, a clip 199 or other suitable attachment means can be used to secure the fan component or module 186 to clothing about the user or wearer's waist.

The present invention also contemplates that all of the non-sterile components of the personal protection and ventilation system described above (e.g., the helmet 190, the air tube 184, the fan module 186, the light source 188, and any accessories attached thereto) may be reusable. In this regard, to minimize the risk of contamination or exposure to pathogens that cause healthcare-associated infections (HAIs), the non-sterile components can, in some embodiments, only be used for one day to reduce the risk of contamination. However, in addition to contemplating daily-use non-sterile components, the present invention also contemplates that the helmet 190, the air tube 184, the fan module 186, the light source 188, and any accessories attached thereto may be coated with an antimicrobial coating. The longer-term use fan module charging unit 270 may also be coated with an antimicrobial coating. The antimicrobial coating can have a thickness ranging from about 0.01 micrometers to about 500 micrometers, such as from about 0.1 micrometers to about 250 micrometers, such as from about 1 micrometer to about 100 micrometers. Such coatings do not increase the weight of the non-sterile components significantly and can also be optically. Further, the antimicrobial coating is not negatively impacted by heat associated with the light source 188, humidity, or UV light and is also biocompatible, biostable, and non-toxic. In one particular embodiment, the antimicrobial coating can be an antimicrobial parylene coating such as Specialty Coating Systems' MICRORESIST parylene coating. Further, the antimicrobial coating can achieve a greater than log 5 kill effectiveness on *E. coli* after 7 days and after 15 days.

II. Sterile Components (Gown With Hood and Visor)

In addition to the non-sterile components described above, as shown in FIGS. 3-4 and 10-13, the system can also include one or more sterile components that can include a disposable surgical gown 101. The gown 101 can include a separate or integral hood 178 and visor 180. As shown in FIGS. 3 and 17A-17C, the helmet 190 and the hood 178 of the surgical gown can be connected to each other during donning via inserting the clips or tabs 210 on the interior sides of the visor 180 of the hood 178 into the receiving tabs 208 on the helmet 190.

Figure 10:
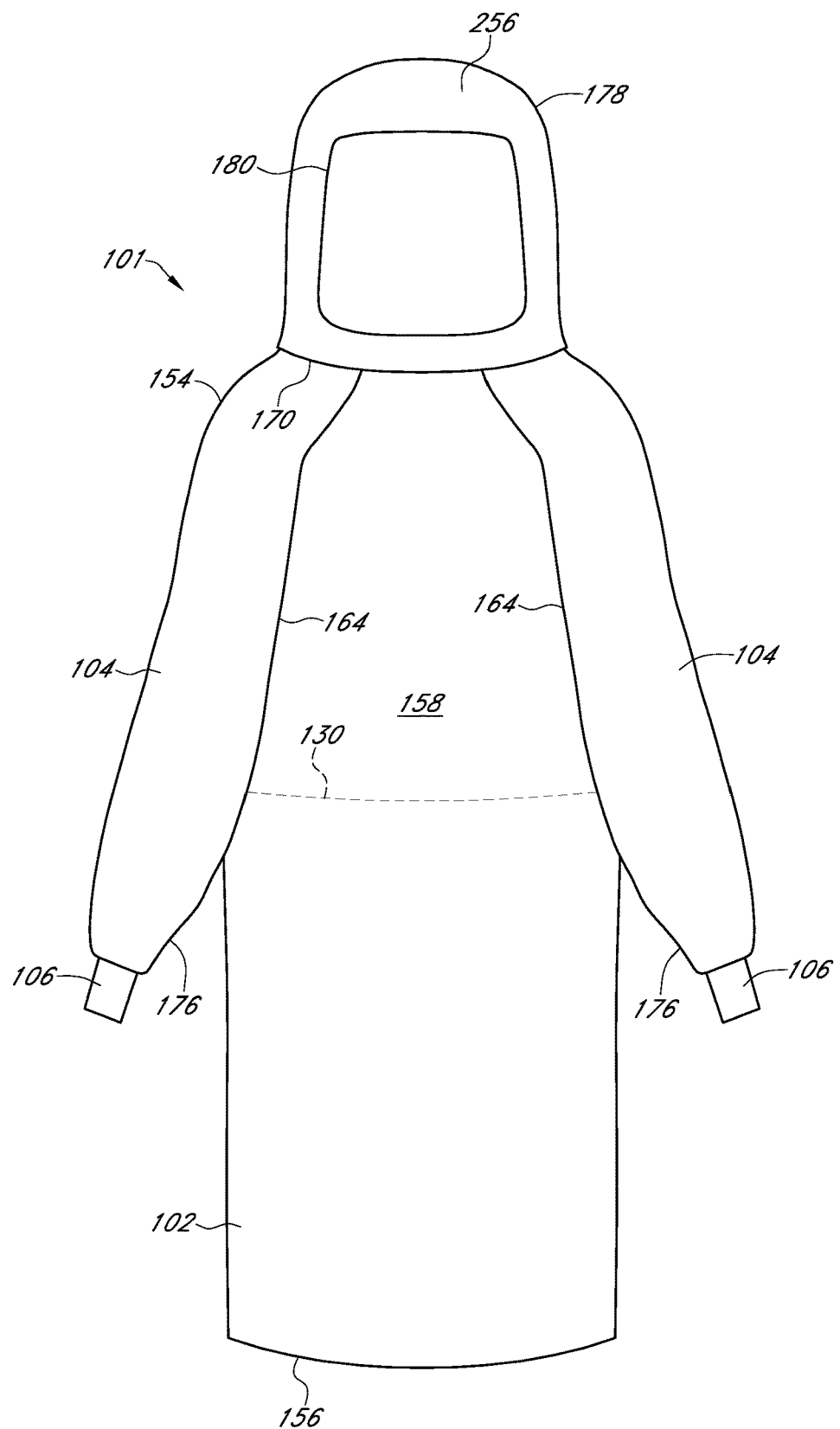
FIG. 10 illustrates a front view of one embodiment of a disposable surgical gown contemplated by the personal protection and ventilation system of the present invention.

FIG. 10 illustrates a front of the disposable surgical gown 101 that is shown folded in FIG. 4. The disposable surgical gown includes a front 158 and a rear 160 that can be worn by medical personnel during a surgical procedure, such as an orthopedic surgical procedure or any other procedure where protection from bodily fluids, bone fragments, etc. is desired. The disposable surgical gown 101 has a waist portion 130 defined between a proximal end 154 and a distal end 156, where the proximal end 154 and the distal end 156 define a front panel 102. As shown, the proximal end 154 includes a hood 178 with a visor 180, while the distal end 156 defines a portion of the gown 101 that is closest to the wearer's feet. As shown in FIG. 10, the hood 178 can be integral with the gown 101 such that the gown 101 and hood 178 form a single garment, where the hood 178 can be sewn to the gown 101 at seam 170. On the other hand, as shown in FIG. 12, in some embodiments, the hood 178 can be a separate component from the surgical gown 101, where the hood 178 can be tucked into the surgical gown 101 inside collar 110. The gown 101 also includes sleeves 104 and cuffs 106. The front panel 102, sleeves 104, and hood 178 can be formed from a laminate of an elastic film and nonwoven materials, as discussed in more detail below. Further, the sleeves 104 can be raglan sleeves, which means that each sleeve 104 extends fully to the collar 110 (see FIG. 12), where a front diagonal seam 164 extends from the underarm up to the collarbone of the wearer and a rear diagonal seam 166 (see FIG. 11) extends from the underarm up to the collarbone of the wearer to attach the sleeves 104 to the front panel 102 and rear panels 120 and 122 of the gown 101. The front diagonal seams 164 and the rear diagonal seams 166 of the sleeves 104 can be sewn to the front panel 102 and rear panels 120 and 122 of the gown. Further, the each sleeve 104 can include a seam 176 that can extend from the underarm area down to the cuff 104, where such sleeves 176 can be seamed thermally so that the sleeves 104 pass ASTM-1671 "Standard Test Method for Resistance of Materials Used in Protective Clothing to Penetration by Blood-Borne Pathogens Using Phi-X174 Bacteriophage Penetration as a Test System."

Figure 11:
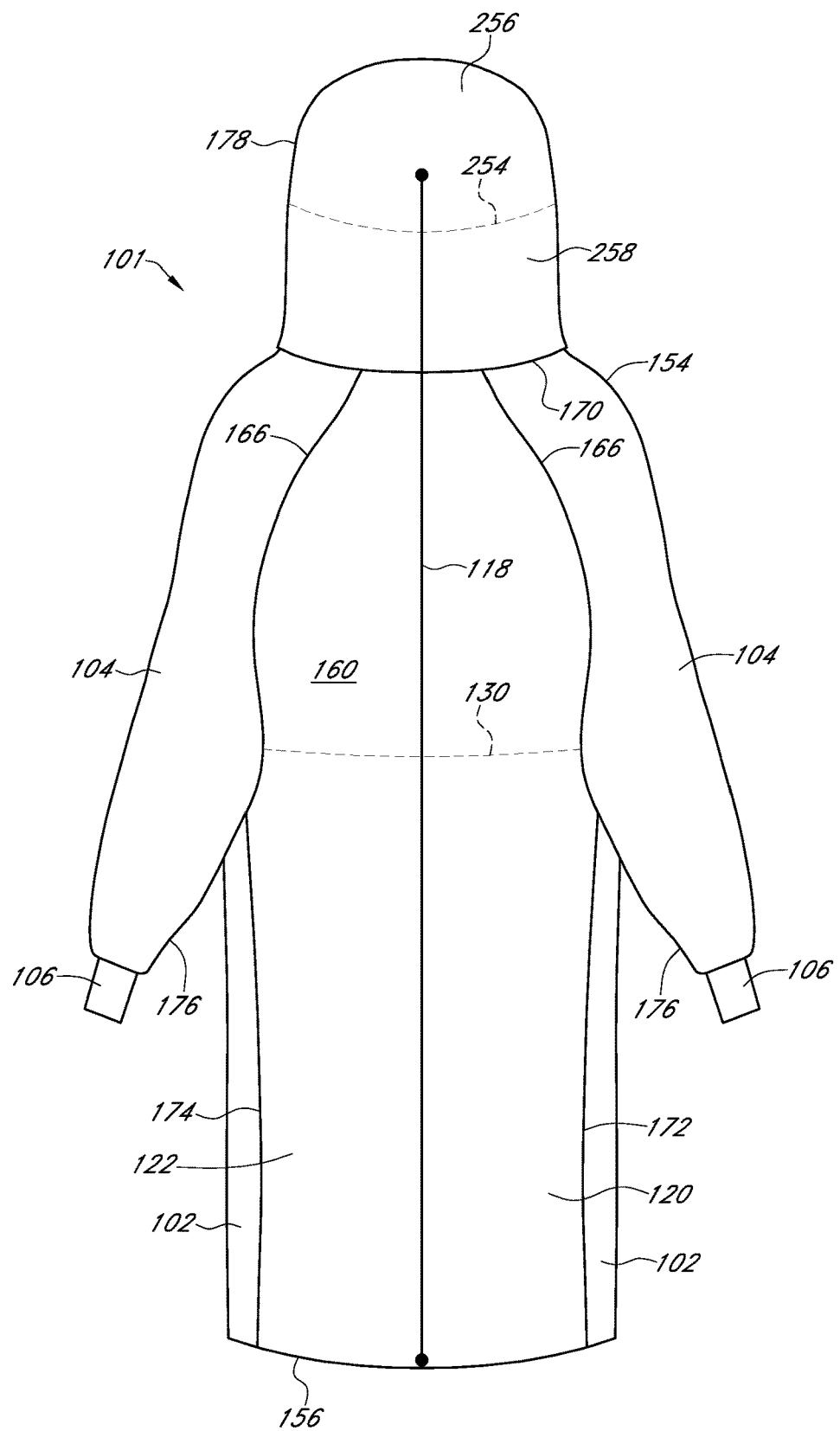
FIG. 11 illustrates a rear view of one embodiment of the disposable surgical of FIG. 10.
Figure 12:
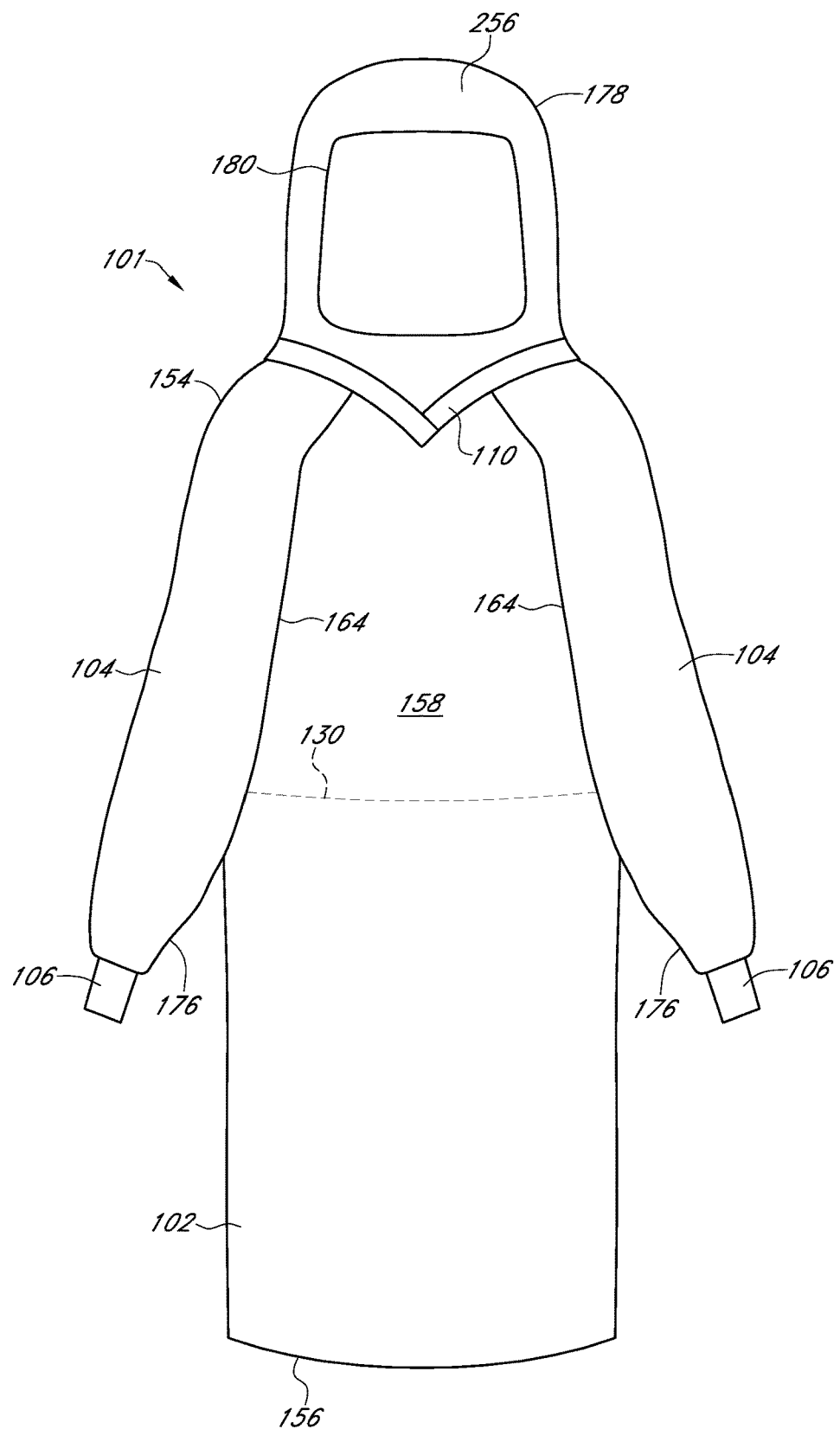
FIG. 12 illustrates a front view of another embodiment of a disposable surgical gown contemplated by the personal protection and ventilation system of the present invention.
Figure 13:
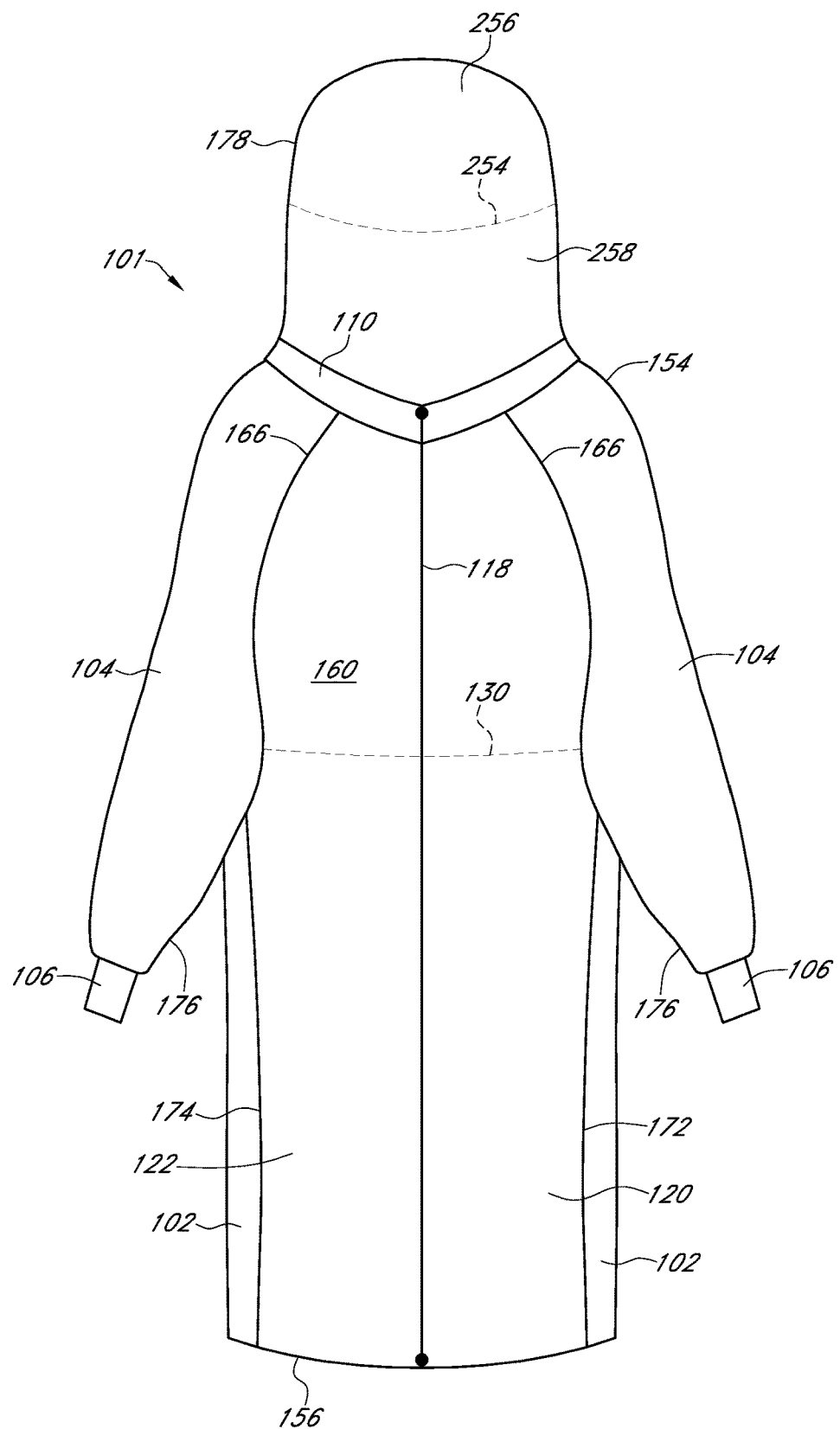
FIG. 13 illustrates a rear view of the disposable surgical gown of FIG. 12.

FIG. 11 illustrates a rear of the disposable surgical gown 101. The proximal end 154 and the distal end 156 define a first rear panel 120 and a second rear panel 122. The first rear panel 120 and second rear panel 122 can be formed of a laminate of nonwoven materials, as discussed in more detail below. Further, as shown in FIG. 11, the hood 178 can be integral with the gown 101 such that the gown 101 and hood 178 form a single garment, where the hood 178 can be sewn to the gown 101 at seam 170. On the other hand, as shown in FIG. 13, in some embodiments, the hood 178 can be a separate component from the surgical gown 101, where the hood 178 can be tucked into the surgical gown 101 inside collar 110. In addition, as shown in FIGS. 11 and 13, the hood 178 can include a first portion 256 and a second portion 256 as separated by a seam 254, where such the materials used to form the first and second portions 258 materials will be discussed in more detail below, although, in some embodiments, it is to be understood that the hood 178 can be formed entirely of a first material 256. Further, the first rear panel 120 can be sewn to the front panel 102 at a seam 172, while the second rear panel 122 can be sewn to the front panel 102 at a seam 174, where the first rear panel 120 can be ultrasonically bonded to the front panel 102 at seam 172 and the second rear panel 122 can be ultrasonically bonded to the front panel 102 at seam 174, where the ultrasonic bonding results in seams 172 and 174 that have improved liquid barrier protection than sewn seams. For instance, such ultrasonic bonding of the rear panels 120 and 122 to the front panel 102 can result in seams 172 and 174 that can have a hydrohead ranging from about 25 cm to about 100 cm, such as from about 30 cm to about 75 cm, such as from about 40 cm to about 60 cm, while sewn seams only have a hydrohead of about 7 cm, where the hydrohead is determined by providing a clear open-ended tube and clamping the seamed material over the bottom end, filling the tube slowly with water from its top end, and measuring how high the column of water is before water passes through the bottom end of the tube. Further, a rear fastening means 118 such as zipper can be used to secure the gown 101 once it is worn by the wearer. Depending on whether the hood 178 is integral with the gown 101 or separate from the gown 101, the fastening means 118 can extend into the area of the hood 178 (see FIG. 11) or can end at the collar 110 (see FIG. 13).

Figure 14:
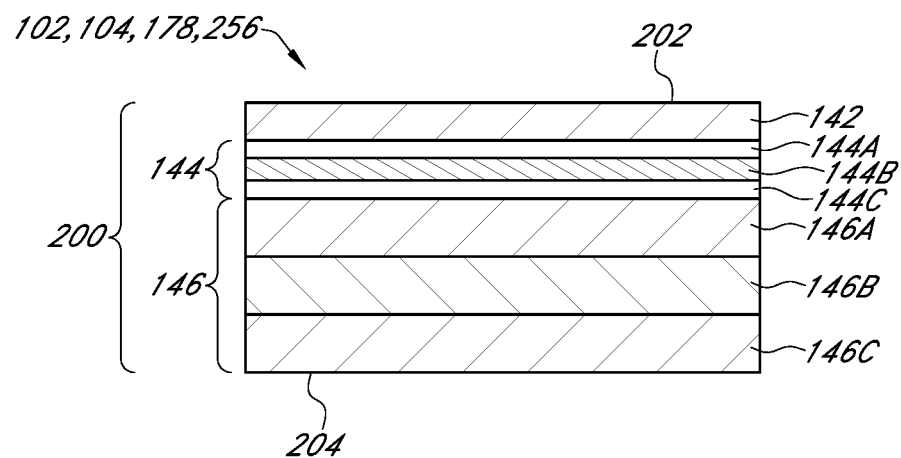
FIG. 14 illustrates a cross-sectional view of one embodiment of a first material used in forming the front panel, sleeves, and hood of the disposable surgical gown of the present invention.

FIG. 14 illustrates a cross-sectional view of a first material 200 which can be used to form the front panel 102, the sleeves 104, and the hood 178 of the surgical gown 101 of FIGS. 4 and 10-13, where the first material 200 passes ASTM-1671 "Standard Test Method for Resistance of Materials Used in Protective Clothing to Penetration by Blood-Borne Pathogens Using Phi-X174 Bacteriophage Penetration as a Test System." In some embodiments, the entire hood 178 can be formed from the first material 200, while, in other embodiments, as shown in FIGS. 10-13, the first portion 256 of the hood 178, which encompasses the entire hood 178 at the front 158 of the gown 101 and the portion of the hood 178 above seam 254 on the rear of the gown 160 and can be formed from the first material 200, while the second portion 258 of the hood can be formed from a second material 300 as discussed in more detail below. The first material 200 can be a laminate that includes an outer spunbond layer 142, an elastic film 144 containing an first skin layer 144A and a second skin layer 144C with a core layer 144B disposed therebetween, and a spunbond-meltblown-spunbond laminate 146 containing a spunbond layer 146A and a spunbond layer 146C with a meltblown layer 146B disposed therebetween. The outer spunbond layer 142 can form an outer-facing surface 202 of the front panel 102 on the front 158 of the gown 101, the sleeves 104, and the hood 178, while the spunbond layer 146C of the SMS laminate 146 can form the body-facing surface or inner-facing surface 204 of the front panel 102 and the sleeves 104 of the surgical gown 101 as well as the hood 178. As discussed in more detail below, the outer spunbond layer 142 and one or more layers of the SMS laminate 146 can include a slip additive to enhance the softness and comfort of the first material 200, while one or more layers of the elastic film 144 can include a fluorochemical additive to enhance the barrier performance of the first material 200. The overall spunbond-film-SMS laminate arrangement of the first material 200 contributes to the moisture vapor breathability of the surgical gown 101 while providing impermeability to air to protect the wearer from exposure to blood, viruses, bacteria, and other harmful contaminants. In other words, the first material 200 allows for an air volumetric flow rate ranging that is less than about 1 standard cubic feet per minute (scfm), such as less than about 0.5 scfm, such as less than about 0.25 scfm, such as less than about 0.1 scfm, such as 0 scfm, as determined at 1 atm (14.7 psi) and 20° C. (68° F.).

Figure 15:
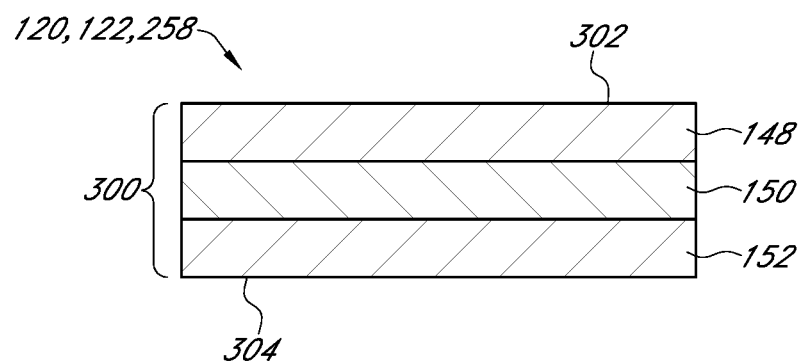
FIG. 15 illustrates a cross-sectional view of one embodiment of a second material used in forming the first rear panel and the second rear panel of the disposable surgical gown of the present invention.

FIG. 15 illustrates a second material 300 that can be used to form the surgical gown 101 of FIGS. 4 and 10-13, where the second material 300 can form the first rear panel 120 and the second rear panel 122. Further, in some embodiments as shown in FIGS. 11 and 13, the second portion 258 of the hood 178 below seam 254 on the rear of the gown 160 can be formed from the second material 300 to provide some breathability to the second or lower portion 258 of the hood 178. The second material 300 can be a laminate that includes a first spunbond layer 148, a meltblown layer 150, and a second spunbond layer 152. The first spunbond layer 148 can form an outer-facing surface 302 of the first rear panel 120 and the second rear panel 122 of the surgical gown 101, while the second spunbond layer 152 can form the body-facing surface or inner-facing surface 304 of the first rear panel 120 and the second rear panel 122 of the surgical gown 101. As discussed in more detail below, the spunbond layers 148 and 152 can include a slip additive to enhance the softness and comfort of the second material 300, while the overall spunbond-meltblown-spunbond (SMS) laminate arrangement of the second material contributes to the air breathability of the surgical gown 101.

The various components of the disposable surgical gown 101 of the personal protection and ventilation system 100 of the present invention are discussed in more detail below. As an initial matter, it is to be understood that any of the spunbond layers, meltblown layers, or elastic film layers of the first material 200 and/or the second material 300 can include pigments to impart the gown 101 with a gray color, which provides anti-glare and light reflectance properties, which, in turn, can provide a better visual field during surgeries or other procedures where operating room lighting can result in poor visual conditions, resulting in glare that causes visual discomfort, and leads to fatigue of operating room staff during surgical procedures.

For instance, examples of suitable pigments used to arrive at the desired gray pigment for the gown include, but are not limited to, titanium dioxide (e.g., SCC 11692 concentrated titanium dioxide), zeolites, kaolin, mica, carbon black, calcium oxide, magnesium oxide, aluminum hydroxide, and combinations thereof. In certain cases, for instance, each of the various individual layers of the gown materials 200 and 300 can include titanium dioxide in an amount ranging from about 0.1 wt. % to about 10 wt. %, in some embodiments, from about 0.5 wt. % to about 7.5 wt. %, and in some embodiments, from about 1 wt. % to about 5 wt. % based on the total weight of the individual layer. The titanium dioxide can have a refractive index ranging from about 2.2 to about 3.2, such as from about 2.4 to about 3, such as from about 2.6 to about 2.8, such as about 2.76, to impart the material 200 with the desired light scattering and light absorbing properties. Further, each of the various individual layers of the gown materials 200 and 300 can also include carbon black in an amount ranging from about 0.1 wt. % to about 10 wt. %, in some embodiments, from about 0.5 wt. % to about 7.5 wt. %, and in some embodiments, from about 1 wt. % to about 5 wt. % based on the total weight of the individual layer. The carbon black can have a refractive index ranging from about 1.2 to about 2.4, such as from about 1.4 to about 2.2, such as from about 1.6 to about 2 to impart the material 200 with the desired light scattering and light absorbing properties. Each of the various individual layers of the gown materials 200 and 300 can also include a blue pigment in an amount ranging from about 0.1 wt. % to about 10 wt. %, in some embodiments, from about 0.5 wt. % to about 7.5 wt. %, and in some embodiments, from about 1 wt. % to about 5 wt. % based on the total weight of the individual layer. The combination of the carbon black and blue pigment improves the ability of the nonwoven materials and film of the present invention to absorb light.

As a result of the incorporation of one or more of the aforementioned pigments into the gown 101 materials, the first material 200 and/or the second material 300 can thus be a sufficient shade of gray to prevent glare. Gray is an imperfect absorption of the light or a mixture of black and white, where it is to be understood that although black, white, and gray are sometimes described as achromatic or hueless colors, a color may be referred to as "black" if it absorbs all frequencies of light. That is, an object that absorbs all wavelengths of light that strike it so that no parts of the spectrum are reflected is considered to be black. Black is darker than any color on the color wheel or spectrum. In contrast, white is lighter than any color on the color wheel or spectrum. If an object reflects all wavelengths of light equally, that object is considered to be white.

A. Front Panel, Sleeves, and Hood

As mentioned above, the front panel 102, sleeves 104, and hood 178 (e.g., all of the hood 178 or at least the first portion 256 of the hood 178 as described above) of the gown 101 can be formed from a first material 200. The first material 200 can be a stretchable elastic breathable barrier material that renders the aforementioned sections of the gown 101 impervious to bodily fluids and other liquids while still providing satisfactory levels of moisture vapor breathability and/or moisture vapor transmission and stretchabiilty. The first material 200 can include a combination of a film, which can serve as the key barrier and elastic component of the surgical gown 101, and one or more nonwoven layers (e.g., spunbond layers, meltblown layers, a combination thereof, etc.) to provide softness and comfort. The film can be configured to exhibit elastic properties such that the film maintains its fluid barrier characteristics even when elongated in the machine direction by amounts at least as twice as high as currently available gowns such that the gown 101 passes ASTM-1671 "Standard Test Method for Resistance of Materials Used in Protective Clothing to Penetration by Blood-Borne Pathogens Using Phi-X174 Bacteriophage Penetration as a Test System." Meanwhile, as a result of the inclusion of the nonwoven layers in conjunction with the elastic film, the overall first material 200 can have an increased bending modulus to achieve the desired pliability and softness which results in a material that is comfortable to the wearer. As discussed above, in one particular embodiment, the first material 200 can include an outer spunbond layer 142, a spunbond-meltblown-spunbond laminate 146, and an elastic film 144 positioned therebetween. The outer spunbond layer 142 can form an outer-facing surface 202 of the front panel 102, sleeves 104, and hood 178 of the surgical gown 101, while one of the spunbond layers of the SMS laminate 146 can form the body-facing surface or inner-facing surface 204 of the front panel 102, sleeves 104, and hood 178 of the surgical gown 101. Further, the outer spunbond layer 142 and one or more layers of the SMS laminate 146 can include a slip additive to achieve the desired softness, while the film 144 can include a fluorochemical additive to increase the surface energy of the elastic film 144 and enhance the ability of the elastic film 144 to serve as a barrier to bodily fluids and tissues, including fatty oils that may be generated during very invasive surgeries as a result of the maceration of fatty tissue. Each of these components of the first material 200 is described in more detail below.

i. Outer Spunbond Layer

The outer spunbond layer 142 can be formed from any suitable polymer that provides softness, stretch, and pliability to the first material 200. For instance, the outer spunbond layer 142 can be formed from a semi-crystalline polyolefin. Exemplary polyolefins may include, for instance, polyethylene, polypropylene, blends and copolymers thereof. In one particular embodiment, a polyethylene is employed that is a copolymer of ethylene and an α-olefin, such as a $C_3$-$C_{20}$ α-olefin or $C_3$-$C_{12}$ α-olefin. Suitable α-olefins may be linear or branched (e.g., one or more $C_1$-$C_3$ alkyl branches, or an aryl group). Specific examples include 1-butene; 3-methyl-1-butene; 3,3-dimethyl-1-butene; 1-pentene; 1-pentene with one or more methyl, ethyl or propyl substituents; 1-hexene with one or more methyl, ethyl or propyl substituents; 1-heptene with one or more methyl, ethyl or propyl substituents; 1-octene with one or more methyl, ethyl or propyl substituents; 1-nonene with one or more methyl, ethyl or propyl substituents; ethyl, methyl or dimethyl-substituted 1-decene; 1-dodecene; and styrene. Particularly desired α-olefin co-monomers are 1-butene, 1-hexene and 1-octene. The ethylene content of such copolymers may be from about 60 mole % to about 99 mole %, in some embodiments from about 80 mole % to about 98.5 mole %, and in some embodiments, from about 87 mole % to about 97.5 mole %. The α-olefin content may likewise range from about 1 mole % to about 40 mole %, in some embodiments from about 1.5 mole % to about 15 mole %, and in some embodiments, from about 2.5 mole % to about 13 mole %.

The density of the polyethylene may vary depending on the type of polymer employed, but generally ranges from 0.85 to 0.96 grams per cubic centimeter ("g/cm$^3$"). Polyethylene "plastomers", for instance, may have a density in the range of from 0.85 to 0.91 g/cm$^3$. Likewise, "linear low density polyethylene" ("LLDPE") may have a density in the range of from 0.91 to 0.940 g/cm$^3$; "low density polyethylene" ("LDPE") may have a density in the range of from 0.910 to 0.940 g/cm$^3$; and "high density polyethylene" ("HDPE") may have density in the range of from 0.940 to 0.960 g/cm$^3$. Densities may be measured in accordance with ASTM 1505. Particularly suitable ethylene-based polymers for use in the present invention may be available under the designation EXACT™ from ExxonMobil Chemical Company of Houston, Tex. Other suitable polyethylene plastomers are available under the designation ENGAGE™ and AFFINITY™ from Dow Chemical Company of Midland, Mich. Still other suitable ethylene polymers are available from The Dow Chemical Company under the designations DOWLEX™ (LLDPE) and ATTANE™ (ULDPE). Other suitable ethylene polymers are described in U.S. Pat. No. 4,937,299 to Ewen et al.; U.S. Pat. No. 5,218,071 to Tsutsui et al.; U.S. Pat. No. 5,272,236 to Lai et at; and U.S. Pat. No. 5,278,272 to Lai et al., which are incorporated herein in their entirety by reference thereto for all purposes.

Of course, the outer spunbond layer 142 of the first material 200 is by no means limited to ethylene polymers. For instance, propylene polymers may also be suitable for use as a semi-crystalline polyolefin. Suitable propylene polymers may include, for instance, polypropylene homopolymers, as well as copolymers or terpolymers of propylene with an α-olefin (e.g., $C_3$-$C_{20}$) comonomer, such as ethylene, 1-butene, 2-butene, the various pentene isomers, 1-hexene, 1-octene, 1-nonene, 1-decene, 1-unidecene, 1-dodecene, 4-methyl-1-pentene, 4-methyl-1-hexene, 5-methyl-1-hexene, vinylcyclohexene, styrene, etc. The comonomer content of the propylene polymer may be about 35 wt. % or less, in some embodiments from about 1 wt. % to about 20 wt. %, in some embodiments, from about 2 wt. % to about 15 wt. %, and in some embodiments from about 3 wt. % to about 10 wt. %. The density of the polypropylene (e.g., propylene/α-olefin copolymer) may be 0.95 grams per cubic centimeter ($g/cm^3$) or less, in some embodiments, from 0.85 to 0.92 $g/cm^3$, and in some embodiments, from 0.85 $g/cm^3$ to 0.91 $g/cm^3$. In one particular embodiment, the outer spunbond layer 142 can include a copolymer of polypropylene and polyethylene. The polypropylene can have a refractive index ranging from about 1.44 to about 1.54, such as from about 1.46 to about 1.52, such as from about 1.48 to about 1.50, such as about 1.49, while the polyethylene can have a refractive index ranging from about 1.46 to about 1.56, such as from about 1.48 to about 1.54, such as from about 1.50 to about 1.52, such as about 1.51, to impart the material 200 with the desired light scattering and light absorbing properties.

Suitable propylene polymers are commercially available under the designations VISTAMAXX™ from ExxonMobil Chemical Co. of Houston, Tex.; FINA™ (e.g., 8573) from Atofina Chemicals of Feluy, Belgium; TAFMER™ available from Mitsui Petrochemical Industries; and VERSIFY™ available from Dow Chemical Co. of Midland, Mich. Other examples of suitable propylene polymers are described in U.S. Pat. No. 6,500,563 to Datta et al.; U.S. Pat. No. 5,539,056 to Yang et al.; and U.S. Pat. No. 5,596,052 to Resconi et al., which are incorporated herein in their entirety by reference thereto for all purposes.

Any of a variety of known techniques may generally be employed to form the polyolefins. For instance, olefin polymers may be formed using a free radical or a coordination catalyst (e.g., Ziegler-Natta or metallocene). Metallocene-catalyzed polyolefins are described, for instance, in U.S. Pat. No. 5,571,619 to McAlpin et at; U.S. Pat. No. 5,322,728 to Davey et al.; U.S. Pat. No. 5,472,775 to Obijeski et al.; U.S. Pat. No. 5,272,236 to Lai et al.; and U.S. Pat. No. 6,090,325 to Wheat et al., which are incorporated herein in their entirety by reference thereto for all purposes.

The melt flow index (MI) of the polyolefins may generally vary, but is typically in the range of about 0.1 grams per 10 minutes to about 100 grams per 10 minutes, in some embodiments from about 0.5 grams per 10 minutes to about 30 grams per 10 minutes, and in some embodiments, about 1 to about 10 grams per 10 minutes, determined at 190° C. The melt flow index is the weight of the polymer (in grams) that may be forced through an extrusion rheometer orifice (0.0825-inch diameter) when subjected to a force of 2160 grams in 10 minutes at 190° C., and may be determined in accordance with ASTM Test Method D1238-E.

In addition to a polyolefin, the outer spunbond layer 142 can also include a slip additive to enhance the softness of the outer spunbond layer 142. The slip additive can also reduce the coefficient of friction and increase the hydrohead of the outer spunbond layer 142 of the front panel 102 and the sleeves 104. Such a reduction in the coefficient of friction lessens the chance of the gown 101 being cut or damaged due to abrasions and also prevents fluids from seeping through the first material 200. Instead, at least in part due to the inclusion of the slip additive, fluid that contacts the outer-facing surface 202 of the gown 101 can remain in droplet form and run vertically to the distal end 156 of the gown 101 and onto the floor. The slip additive can also reduce the glare of the first material 200 in the operating room by reducing the light reflectance of the first material and can also render the first material 200 more opaque than the standard gown material when contacted with fats and lipids during surgery, where the standard gown material turns transparent upon contact with fats and lipids, which can result in the wearer having some concern that the barrier properties of a standard gown have been compromised.

The slip additive can function by migrating to the surface of the polymer used to form the outer spunbond layer 142, where it can provide a coating that reduces the coefficient of friction of the outer-facing surface 202 of the first material 200. Variants of fatty acids can be used as slip additives. For example, the slip additive can be erucamide, oleamide, stearamide, behenamide, oleyl palmitamide, stearyl erucamide, ethylene bis-oleamide, N,N'-Ethylene Bis(Stearamide) (EBS), or a combination thereof. Further, the slip additive have a refractive index ranging from about 1.42 to about 1.52, such as from about 1.44 to about 1.50, such as from about 1.46 to about 1.48, such as about 1.47, to impart the material 200 with the desired light scattering and light absorbing properties by reducing the refractive index. The slip additive can be present in the outer spunbond layer 142 in an amount ranging from about 0.1 wt. % to about 4 wt. %, such as from about 0.25 wt. % to about 3 wt. %, such as from about 0.5 wt. % to about 2 wt. % based on the total weight of the outer spunbond layer 142. In one particular embodiment, the slip additive can be present in an amount of about 1 wt. % based on the total weight of the outer spunbond layer 142.

In addition to the polyolefin and slip additive, the outer spunbond layer 142 can also include one or more pigments to help achieve the desired gray color of the gown 101. Examples of suitable pigments include, but are not limited to, titanium dioxide (e.g., SCC 11692 concentrated titanium dioxide), zeolites, kaolin, mica, carbon black, calcium oxide, magnesium oxide, aluminum hydroxide, and combinations thereof. In certain cases, for instance, the outer spunbond layer 142 can include titanium dioxide in an amount ranging from about 0.1 wt. % to about 10 wt. %, in some embodiments, from about 0.5 wt. % to about 7.5 wt. %, and in some embodiments, from about 1 wt. % to about 5 wt. % based on the total weight of the outer spunbond layer 142. The titanium dioxide can have a refractive index ranging from about 2.2 to about 3.2, such as from about 2.4 to about 3, such as from about 2.6 to about 2.8, such as about 2.76, to impart the material 200 with the desired light scattering and light absorbing properties. Further, the outer spunbond layer 142 can also include carbon black in an amount ranging from about 0.1 wt. % to about 10 wt. %, in some embodiments, from about 0.5 wt. % to about 7.5 wt. %, and in some embodiments, from about 1 wt. % to about 5 wt. % based on the total weight of the outer spunbond layer 142. The carbon black can have a refractive index ranging from about 1.2 to about 2.4, such as from about 1.4 to about 2.2, such as from about 1.6 to about 2 to impart the material 200 with the desired light scattering and light absorbing properties. The outer spunbond layer 142 can also include a blue pigment in an amount ranging from about 0.1 wt. % to about 10 wt. %, in some embodiments, from about 0.5 wt. % to about 7.5 wt. %, and in some embodiments, from about 1 wt. % to about 5 wt. % based on the total weight of the individual layer. The combination of the carbon black and blue pigment improves the ability of the outer spunbond layer 142 to absorb light.

Regardless of the specific polymer or polymers and additives used to form the outer spunbond layer 142, the outer spunbond layer 142 can have a basis weight ranging from about 5 gsm to about 50 gsm, such as from about 10 gsm to about 40 gsm, such as from about 15 gsm to about 30 gsm. In one particular embodiment, the outer spunbond layer 142 can have a basis weight of about 20 gsm (about 0.6 osy).

ii. Elastic Film

The elastic film 144 of the first material 200 can be formed from any suitable polymer or polymers that are capable of acting as a barrier component in that it is generally impervious, while at the same time providing moisture vapor breathability to the first material 200. The elastic film 144 can be formed from one or more layers of polymers that are melt-processable, i.e., thermoplastic. In one particular embodiment, the elastic film 144 can be a monolayer film. If the film is a monolayer, any of the polymers discussed below in can be used to form the monolayer. In other embodiments, the elastic film 144 can include two, three, four, five, six, or seven layers, where each of the layers can be formed from any of the polymers discussed below, where the one or more layers are formed from the same or different materials. For instance, in one particular embodiment the elastic film 144 can include a core layer 144B disposed between two skin layers, 144A and 144C. Each of these components of the film are discussed in more detail below.

First, the elastic film core layer 144B can be formed from one or more semi-crystalline polyolefins. Exemplary semi-crystalline polyolefins include polyethylene, polypropylene, blends and copolymers thereof. In one particular embodiment, a polyethylene is employed that is a copolymer of ethylene and an α-olefin, such as a $C_3$-$C_{20}$ α-olefin or $C_3$-$C_{12}$ α-olefin. Suitable α-olefins may be linear or branched (e.g., one or more $C_1$-$C_3$ alkyl branches, or an aryl group). Specific examples include 1-butene; 3-methyl-1-butene; 3,3-dimethyl-1-butene; 1-pentene; 1-pentene with one or more methyl, ethyl or propyl substituents; 1-hexene with one or more methyl, ethyl or propyl substituents; 1-heptene with one or more methyl, ethyl or propyl substituents; 1-octene with one or more methyl, ethyl or propyl substituents; 1-nonene with one or more methyl, ethyl or propyl substituents; ethyl, methyl or dimethyl-substituted 1-decene; 1-dodecene; and styrene. Particularly desired α-olefin comonomers are 1-butene, 1-hexene and 1-octene. The ethylene content of such copolymers may be from about 60 mole % to about 99 mole %, in some embodiments from about 80 mole % to about 98.5 mole %, and in some embodiments, from about 87 mole % to about 97.5 mole %. The α-olefin content may likewise range from about 1 mole % to about 40 mole %, in some embodiments from about 1.5 mole % to about 15 mole %, and in some embodiments, from about 2.5 mole % to about 13 mole %.

Particularly suitable polyethylene copolymers are those that are "linear" or "substantially linear." The term "substantially linear" means that, in addition to the short chain branches attributable to comonomer incorporation, the ethylene polymer also contains long chain branches in the polymer backbone. "Long chain branching" refers to a chain length of at least 6 carbons. Each long chain branch may have the same comonomer distribution as the polymer backbone and be as long as the polymer backbone to which it is attached. Preferred substantially linear polymers are substituted with from 0.01 long chain branch per 1000 carbons to 1 long chain branch per 1000 carbons, and in some embodiments, from 0.05 long chain branch per 1000 carbons to 1 long chain branch per 1000 carbons. In contrast to the term "substantially linear", the term "linear" means that the polymer lacks measurable or demonstrable long chain branches. That is, the polymer is substituted with an average of less than 0.01 long chain branch per 1000 carbons.

The density of a linear ethylene/α-olefin copolymer is a function of both the length and amount of the α-olefin. That is, the greater the length of the α-olefin and the greater the amount of α-olefin present, the lower the density of the copolymer. Although not necessarily required, linear polyethylene "plastomers" are particularly desirable in that the content of α-olefin short chain branching content is such that the ethylene copolymer exhibits both plastic and elastomeric characteristics—i.e., a "plastomer." Because polymerization with α-olefin comonomers decreases crystallinity and density, the resulting plastomer normally has a density lower than that of a polyethylene thermoplastic polymer (e.g., LLDPE), which typically has a density (specific gravity) of from about 0.90 grams per cubic centimeter (g/cm$^3$) to about 0.94 g/cm$^3$, but approaching and/or overlapping that of an elastomer, which typically has a density of from about 0.85 g/cm$^3$ to about 0.90 g/cm$^3$, preferably from 0.86 to 0.89. For example, the density of the polypropylene (e.g., propylene/α-olefin copolymer) may be 0.95 grams per cubic centimeter (g/cm$^3$) or less, in some embodiments, from 0.85 to 0.92 g/cm$^3$, and in some embodiments, from 0.85 g/cm$^3$ to 0.91 g/cm$^3$. Despite having a density similar to elastomers, plastomers generally exhibit a higher degree of crystallinity, are relatively non-tacky, and may be formed into pellets that are non-adhesive-like and relatively free flowing.

Preferred polyethylenes for use in the present invention are ethylene-based copolymer plastomers available under the designation EXACT™ from ExxonMobil Chemical Company of Houston, Tex. Other suitable polyethylene plastomers are available under the designation ENGAGE™ and AFFINITY™ from Dow Chemical Company of Midland, Mich. An additional suitable polyethylene-based plastomer is an olefin block copolymer available from Dow Chemical Company of Midland, Mich. under the trade designation INFUSE™, which is an elastomeric copolymer of polyethylene. Still other suitable ethylene polymers are low density polyethylenes (LDPE), linear low density polyethylenes (LLDPE) or ultralow linear density polyethylenes (ULDPE), such as those available from The Dow Chemical Company under the designations ASPUN™ (LLDPE), DOWLEX™ (LLDPE) and ATTANE™ (ULDPE). Other suitable ethylene polymers are described in U.S. Pat. No. 4,937,299 to Ewen et al., U.S. Pat. No. 5,218,071 to Tsutsui et al., U.S. Pat. No. 5,272,236 to Lai et at, and U.S. Pat. No. 5,278,272 to Lai et al., which are incorporated herein in their entirety by reference thereto for all purposes.

Of course, the elastic film core layer 144B of the present invention is by no means limited to ethylene polymers. For instance, propylene plastomers may also be suitable for use in the film. Suitable plastomeric propylene polymers may include, for instance, polypropylene homopolymers, copolymers or terpolymers of propylene, copolymers of propylene with an α-olefin (e.g., $C_3$-$C_{20}$) comonomer, such as ethylene, 1-butene, 2-butene, the various pentene isomers, 1-hexene, 1-octene, 1-nonene, 1-decene, 1-unidecene, 1-dodecene, 4-methyl-1-pentene, 4-methyl-1-hexene, 5-methyl-1-hexene, vinylcyclohexene, styrene, etc. The comonomer content of the propylene polymer may be about 35 wt. % or less, in some embodiments from about 1 wt. % to about 20 wt. %, in some embodiments from about 2 wt. % to about 15 wt. %, and in some embodiments from about 3 wt. % to about 10 wt. %. Preferably, the density of the polypropylene (e.g., propylene/α-olefin copolymer) may be 0.95 grams per cubic centimeter (g/cm³) or less, in some embodiments, from 0.85 to 0.92 g/cm³, and in some embodiments, from 0.85 g/cm³ to 0.91 g/cm³.

Suitable propylene polymers are commercially available under the designations VISTAMAXX™ (e.g., 6102), a propylene-based elastomer from ExxonMobil Chemical Co. of Houston, Tex.; FINA™ (e.g., 8573) from Atofina Chemicals of Feluy, Belgium; TAFMER™ available from Mitsui Petrochemical Industries; and VERSIFY™ available from Dow Chemical Co. of Midland, Mich. Other examples of suitable propylene polymers are described in U.S. Pat. No. 5,539,056 to Yang et al., U.S. Pat. No. 5,596,052 to Resconi et al., and U.S. Pat. No. 6,500,563 to Datta et al., which are incorporated herein in their entirety by reference thereto for all purposes. In one particular embodiment, the elastic film core layer 144B includes polypropylene. The polypropylene can have a refractive index ranging from about 1.44 to about 1.54, such as from about 1.46 to about 1.52, such as from about 1.48 to about 1.50, such as about 1.49 to help impart the material 200 with the desired light scattering and light absorbing properties.

Any of a variety of known techniques may generally be employed to form the semi-crystalline polyolefins. For instance, olefin polymers may be formed using a free radical or a coordination catalyst (e.g., Ziegler-Natta). Preferably, the olefin polymer is formed from a single-site coordination catalyst, such as a metallocene catalyst. Such a catalyst system produces ethylene copolymers in which the comonomer is randomly distributed within a molecular chain and uniformly distributed across the different molecular weight fractions. Metallocene-catalyzed polyolefins are described, for instance, in U.S. Pat. No. 5,272,236 to Lai et al., U.S. Pat. No. 5,322,728 to Davey et al., U.S. Pat. No. 5,472,775 to Obijeski et al., U.S. Pat. No. 5,571,619 to McAlpin et al., and U.S. Pat. No. 6,090,325 to Wheat et al., which are incorporated herein in their entirety by reference thereto for all purposes. Examples of metallocene catalysts include bis(n-butylcyclopentadienyl)titanium dichloride, bis(n-butylcyclopentadienyl)zirconium dichloride, bis(cyclopentadienyl)scandium chloride, bis(indenyl)zirconium dichloride, bis(methylcyclopentadienyl)titanium dichloride, bis(methylcyclopentadienyl) zirconium dichloride, cobaltocene, cyclopentadienyltitanium trichloride, ferrocene, hafnocene dichloride, isopropyl(cyclopentadienyl,-1-flourenyl)zirconium dichloride, molybdocene dichloride, nickelocene, niobocene dichloride, ruthenocene, titanocene dichloride, zirconocene chloride hydride, zirconocene dichloride, and so forth. Polymers made using metallocene catalysts typically have a narrow molecular weight range. For instance, metallocene-catalyzed polymers may have polydispersity numbers ($M_w/M_n$) of below 4, controlled short chain branching distribution, and controlled isotacticity.

The melt flow index (MI) of the semi-crystalline polyolefins may generally vary, but is typically in the range of about 0.1 grams per 10 minutes to about 100 grams per 10 minutes, in some embodiments from about 0.5 grams per 10 minutes to about 30 grams per 10 minutes, and in some embodiments, about 1 to about 10 grams per 10 minutes, determined at 190° C. The melt flow index is the weight of the polymer (in grams) that may be forced through an extrusion rheometer orifice (0.0825-inch diameter) when subjected to a force of 5000 grams in 10 minutes at 190° C., and may be determined in accordance with ASTM Test Method D1238-E.

In addition to a polyolefin such as polypropylene, the elastic film core layer 144B can also include a fluorochemical additive to increase the surface energy of the elastic film 144, which, in turn, increases the imperviousness of the elastic film 144 to bodily fluids and biologic materials such as fatty oils that may be generated during very invasive surgeries. One example of a fluorochemical additive contemplated for use in the core layer 144B is a fluoroalkyl acrylate copolymer such as Unidyne® TG from Daikin. The fluorochemical additive can have a refractive index that is less than about 1.4 in order to lower the refractive index of the elastic film core layer 144B. For instance, the fluorochemical additive can have a refractive index ranging from about 1.2 to about 1.4, such as from about 1.22 to about 1.38, such as from about 1.24 to about 1.36. Without intending to be limited by any particular theory, it is believed that the fluorochemical additive segregates to the surface of the polyolefin film, where a lower refractive index region is formed, which enhances light scattering of the film as compared to films that are free of a fluorochemical additive. Regardless of the particular fluorochemical additive utilized, the fluorochemical additive can be present in the elastic film core layer 144B in an amount ranging from about 0.1 wt. % to about 5 wt. %, such as from about 0.5 wt. % to about 4 wt. %, such as from about 1 wt. % to about 3 wt. % based on the total weight of the elastic film core layer 144B. In one particular embodiment, the fluorochemical additive can be present in an amount of about 1.5 wt. % based on the total weight of the elastic film core layer 144B.

In one embodiment, the elastic film core layer 144B can also include a filler. Fillers are particulates or other forms of material that may be added to the film polymer extrusion blend and that will not chemically interfere with the extruded film, but which may be uniformly dispersed throughout the film. Fillers may serve a variety of purposes, including enhancing film opacity and/or breathability (i.e., vapor-permeable and substantially liquid-impermeable). For instance, filled films may be made breathable by stretching, which causes the polymer to break away from the filler and create microporous passageways. Breathable microporous elastic films are described, for example, in U.S. Pat. No. 5,932,497 to Morman et al., U.S. Pat. Nos. 5,997,981, 6,015,764, and 6,111,163 to McCormack et al., and U.S. Pat. No. 6,461,457 to Taylor et al., which are incorporated herein in their entirety by reference thereto for all purposes. Examples of suitable fillers include, but are not limited to, calcium carbonate, various kinds of clay, silica, alumina, barium carbonate, sodium carbonate, magnesium carbonate, talc, barium sulfate, magnesium sulfate, aluminum sulfate, zeolites, cellulose-type powders, kaolin, mica, carbon, calcium oxide, magnesium oxide, aluminum hydroxide, pulp powder, wood powder, cellulose derivatives, chitin and chitin derivatives. In one particular embodiment, the filler in the core layer 144B can include calcium carbonate, which can provide the elastic film 144, and thus the material 200, with light scattering and light absorbing properties to help reduce glare, particularly after stretching the calcium carbonate-containing core layer 144B, which further increases the opacity and increases the light scattering of the material 200. For instance, the calcium carbonate (or any other suitable filler) can have a refractive index ranging from about 1.60 to about 1.72, such as from about 1.62 to about 1.70, such as from about 1.64 to about 1.68, such as about 1.66, to impart the material 200 with the desired light scattering and light absorbing properties. In certain cases, the filler content of the film may range from about 50 wt. % to about 85 wt. %, in some embodiments, from about 55 wt. % to about 80 wt. %, and in some embodiments, from about 60 wt. % to about 75 wt. % of the elastic film core layer 144*6* based on the total weight of the elastic film core layer 144B.

Further, the elastic film core layer 1446 can also include one or more pigments to help achieve the desired gray color of the gown 101. Examples of suitable pigments include, but are not limited to, titanium dioxide (e.g., SCC 11692 concentrated titanium dioxide), zeolites, kaolin, mica, carbon black, calcium oxide, magnesium oxide, aluminum hydroxide, and combinations thereof. In certain cases, for instance, the elastic film core layer 144B can include titanium dioxide in an amount ranging from about 0.1 wt. % to about 10 wt. %, in some embodiments, from about 0.5 wt. % to about 7.5 wt. %, and in some embodiments, from about 1 wt. % to about 5 wt. % based on the total weight of the core layer 144B. The titanium dioxide can have a refractive index ranging from about 2.2 to about 3.2, such as from about 2.4 to about 3, such as from about 2.6 to about 2.8, such as about 2.76, to impart the material 200 with the desired light scattering and light absorbing properties. Further, the elastic film core layer 1446 can also include carbon black in an amount ranging from about 0.1 wt. % to about 10 wt. %, in some embodiments, from about 0.5 wt. % to about 7.5 wt. %, and in some embodiments, from about 1 wt. % to about 5 wt. % based on the total weight of the core layer 144B. The carbon black can have a refractive index ranging from about 1.2 to about 2.4, such as from about 1.4 to about 2.2, such as from about 1.6 to about 2 to impart the material 200 with the desired light scattering and light absorbing properties. The elastic film core layer 144B can also include a blue pigment in an amount ranging from about 0.1 wt. % to about 10 wt. %, in some embodiments, from about 0.5 wt. % to about 7.5 wt. %, and in some embodiments, from about 1 wt. % to about 5 wt. % based on the total weight of the individual layer. The combination of the carbon black and blue pigment improves the ability of the elastic film core layer 144B to absorb light.

Further, like the elastic film core layer 144B, the elastic film skin layers 144A and 144C that sandwich the elastic film core layer 144B can also be formed from one or more semi-crystalline polyolefins. Exemplary semi-crystalline polyolefins include polyethylene, polypropylene, blends and copolymers thereof. In one particular embodiment, a polyethylene is employed that is a copolymer of ethylene and an α-olefin, such as a $C_3$-$C_{20}$ α-olefin or $C_3$-$C_{12}$ α-olefin. Suitable α-olefins may be linear or branched (e.g., one or more $C_1$-$C_3$ alkyl branches, or an aryl group). Specific examples include 1-butene; 3-methyl-1-butene; 3,3-dimethyl-1-butene; 1-pentene; 1-pentene with one or more methyl, ethyl or propyl substituents; 1-hexene with one or more methyl, ethyl or propyl substituents; 1-heptene with one or more methyl, ethyl or propyl substituents; 1-octene with one or more methyl, ethyl or propyl substituents; 1-nonene with one or more methyl, ethyl or propyl substituents; ethyl, methyl or dimethyl-substituted 1-decene; 1-dodecene; and styrene. Particularly desired α-olefin comonomers are 1-butene, 1-hexene and 1-octene. The ethylene content of such copolymers may be from about 60 mole % to about 99 mole %, in some embodiments from about 80 mole % to about 98.5 mole %, and in some embodiments, from about 87 mole % to about 97.5 mole %. The α-olefin content may likewise range from about 1 mole % to about 40 mole %, in some embodiments from about 1.5 mole % to about 15 mole %, and in some embodiments from about 2.5 mole % to about 13 mole %.

Particularly suitable polyethylene copolymers are those that are "linear" or "substantially linear." The term "substantially linear" means that, in addition to the short chain branches attributable to comonomer incorporation, the ethylene polymer also contains long chain branches in the polymer backbone. "Long chain branching" refers to a chain length of at least 6 carbons. Each long chain branch may have the same comonomer distribution as the polymer backbone and be as long as the polymer backbone to which it is attached. Preferred substantially linear polymers are substituted with from 0.01 long chain branch per 1000 carbons to 1 long chain branch per 1000 carbons, and in some embodiments, from 0.05 long chain branch per 1000 carbons to 1 long chain branch per 1000 carbons. In contrast to the term "substantially linear", the term "linear" means that the polymer lacks measurable or demonstrable long chain branches. That is, the polymer is substituted with an average of less than 0.01 long chain branch per 1000 carbons.

The density of a linear ethylene/α-olefin copolymer is a function of both the length and amount of the α-olefin. That is, the greater the length of the α-olefin and the greater the amount of α-olefin present, the lower the density of the copolymer. Although not necessarily required, linear polyethylene "plastomers" are particularly desirable in that the content of α-olefin short chain branching content is such that the ethylene copolymer exhibits both plastic and elastomeric characteristics—i.e., a "plastomer." Because polymerization with α-olefin comonomers decreases crystallinity and density, the resulting plastomer normally has a density lower than that of a polyethylene thermoplastic polymer (e.g., LLDPE), which typically has a density (specific gravity) of from about 0.90 grams per cubic centimeter ($g/cm^3$) to about 0.94 $g/cm^3$, but approaching and/or overlapping that of an elastomer, which typically has a density of from about 0.85 $g/cm^3$ to about 0.90 $g/cm^3$, preferably from 0.86 to 0.89. For example, the density of the polyethylene plastomer may be 0.91 $g/cm^3$ or less, in some embodiments from about 0.85 $g/cm^3$ to about 0.90 $g/cm^3$, in some embodiments, from 0.85 $g/cm^3$ to 0.88 $g/cm^3$, and in some embodiments, from 0.85 $g/cm^3$ to 0.87 $g/cm^3$. Despite having a density similar to elastomers, plastomers generally exhibit a higher degree of crystallinity, are relatively non-tacky, and may be formed into pellets that are non-adhesive-like and relatively free flowing.

Preferred polyethylenes for use in the present invention are ethylene-based copolymer plastomers available under the designation EXACT™ from ExxonMobil Chemical Company of Houston, Tex. Other suitable polyethylene plastomers are available under the designation ENGAGE™ and AFFINITY™ from Dow Chemical Company of Midland, Mich. An additional suitable polyethylene-based plastomer is an olefin block copolymer available from Dow Chemical Company of Midland, Mich. under the trade designation INFUSE™, which is an elastomeric copolymer of polyethylene. Still other suitable ethylene polymers are low density polyethylenes (LDPE), linear low density polyethylenes (LLDPE) or ultralow linear density polyethylenes (ULDPE), such as those available from The Dow Chemical Company under the designations ASPUN™ (LLDPE), DOWLEX™ (LLDPE) and ATTANE™ (ULDPE). Other suitable ethylene polymers are described in U.S. Pat. No. 4,937,299 to Ewen et al., U.S. Pat. No. 5,218,071 to Tsutsui et al., U.S. Pat. No. 5,272,236 to Lai et at, and U.S. Pat. No. 5,278,272 to Lai et al., which are incorporated herein in their entirety by reference thereto for all purposes.

Of course, the elastic film skin layers 144A and 144C of the present invention are by no means limited to ethylene polymers. For instance, propylene plastomers may also be suitable for use in the film. Suitable plastomeric propylene polymers may include, for instance, polypropylene homopolymers, copolymers or terpolymers of propylene, copolymers of propylene with an α-olefin (e.g., $C_3$-$C_{20}$) comonomer, such as ethylene, 1-butene, 2-butene, the various pentene isomers, 1-hexene, 1-octene, 1-nonene, 1-decene, 1-unidecene, 1-dodecene, 4-methyl-1-pentene, 4-methyl-1-hexene, 5-methyl-1-hexene, vinylcyclohexene, styrene, etc. The comonomer content of the propylene polymer may be about 35 wt. % or less, in some embodiments from about 1 wt. % to about 20 wt. %, in some embodiments from about 2 wt. % to about 15 wt. %, and in some embodiments from about 3 wt. % to about 10 wt. %. The density of the polypropylene (e.g., propylene/α-olefin copolymer) may be 0.95 grams per cubic centimeter (g/cm$^3$) or less, in some embodiments, from 0.85 to 0.92 g/cm$^3$, and in some embodiments, from 0.85 g/cm$^3$ to 0.91 g/cm$^3$. In one particular embodiment, the elastic film skin layers 144A and 144C can include a copolymer of polypropylene and polyethylene. The polypropylene can have a refractive index ranging from about 1.44 to about 1.54, such as from about 1.46 to about 1.52, such as from about 1.48 to about 1.50, such as about 1.49, while the polyethylene can have a refractive index ranging from about 1.46 to about 1.56, such as from about 1.48 to about 1.54, such as from about 1.50 to about 1.52, such as about 1.51, to impart the material 200 with the desired light scattering and light absorbing properties.

Suitable propylene polymers are commercially available under the designations VISTAMAXX™ (e.g., 6102), a propylene-based elastomer from ExxonMobil Chemical Co. of Houston, Tex.; FINA™ (e.g., 8573) from Atofina Chemicals of Feluy, Belgium; TAFMER™ available from Mitsui Petrochemical Industries; and VERSIFY™ available from Dow Chemical Co. of Midland, Mich. Other examples of suitable propylene polymers are described in U.S. Pat. No. 5,539,056 to Yang et al., U.S. Pat. No. 5,596,052 to Resconi et al., and U.S. Pat. No. 6,500,563 to Datta et al., which are incorporated herein in their entirety by reference thereto for all purposes.

Any of a variety of known techniques may generally be employed to form the semi-crystalline polyolefins. For instance, olefin polymers may be formed using a free radical or a coordination catalyst (e.g., Ziegler-Natta). Preferably, the olefin polymer is formed from a single-site coordination catalyst, such as a metallocene catalyst. Such a catalyst system produces ethylene copolymers in which the comonomer is randomly distributed within a molecular chain and uniformly distributed across the different molecular weight fractions. Metallocene-catalyzed polyolefins are described, for instance, in U.S. Pat. No. 5,272,236 to Lai et al., U.S. Pat. No. 5,322,728 to Davey et al., U.S. Pat. No. 5,472,775 to Obijeski et al., U.S. Pat. No. 5,571,619 to McAlpin et al., and U.S. Pat. No. 6,090,325 to Wheat et al., which are incorporated herein in their entirety by reference thereto for all purposes. Examples of metallocene catalysts include bis(n-butylcyclopentadienyl)titanium dichloride, bis(n-butylcyclopentadienyl)zirconium dichloride, bis(cyclopentadienyl)scandium chloride, bis(indenyl)zirconium dichloride, bis(methylcyclopentadienyl)titanium dichloride, bis(methylcyclopentadienyl) zirconium dichloride, cobaltocene, cyclopentadienyltitanium trichloride, ferrocene, hafnocene dichloride, isopropyl(cyclopentadienyl,-1-flourenyl)zirconium dichloride, molybdocene dichloride, nickelocene, niobocene dichloride, ruthenocene, titanocene dichloride, zirconocene chloride hydride, zirconocene dichloride, and so forth. Polymers made using metallocene catalysts typically have a narrow molecular weight range. For instance, metallocene-catalyzed polymers may have polydispersity numbers ($M_w/M_n$) of below 4, controlled short chain branching distribution, and controlled isotacticity.

The melt flow index (MI) of the semi-crystalline polyolefins may generally vary, but is typically in the range of about 0.1 grams per 10 minutes to about 100 grams per 10 minutes, in some embodiments from about 0.5 grams per 10 minutes to about 30 grams per 10 minutes, and in some embodiments, about 1 to about 10 grams per 10 minutes, determined at 190° C. The melt flow index is the weight of the polymer (in grams) that may be forced through an extrusion rheometer orifice (0.0825-inch diameter) when subjected to a force of 5000 grams in 10 minutes at 190° C., and may be determined in accordance with ASTM Test Method D1238-E.

In addition, it is noted that the elastic film skin layers 144A and 144C are free of the fluorochemical additive that is present in the elastic film core layer 144B. As a result, the skin layers 144A and 144C have a higher refractive index than the elastic film core layer 144B, as the fluorochemical additive tends to lower the refractive index of the core layer 144B. The resulting difference in refractive indices at the interfaces between the core layer 144B and the skin layers 144A and 144C of the elastic film 144 is thought to enhance light scattering, which can result in a high level of opacity and a low level of light reflection (e.g., reduced glare).

In any event, regardless of the number of layers present in the elastic film 144 and regardless of the specific polymer or polymers and additives used to form the elastic film 144, the elastic film 144 can have a basis weight ranging from about 5 gsm to about 50 gsm, such as from about 10 gsm to about 40 gsm, such as from about 15 gsm to about 30 gsm. In one particular embodiment, the elastic film 144 can have a basis weight of about 20 gsm (about 0.6 osy).

iii. Spunbond Meltblown Spunbond (SMS) Laminate

The first material 200 also includes an SMS laminate 146 that is attached to the skin layer 144C of the elastic film 144. One of the spunbond layers 146C of the SMS laminate 146 can form the inner-facing surface 204 of the first material 200 of the gown 101, which is used to form the front panel 102 on the front 158 of the gown 101, the sleeves 104 and the hood 178. Further, it is to be understood that the spunbond layer 146A, which is adjacent the skin layer 144C, the spunbond layer 146C, and the meltblown layer 146B disposed therebetween can be formed from any of the polymers (e.g., polyolefins) mentioned above with respect to the outer spunbond layer 142. In other words, the SMS laminate 146 can be formed from any suitable polymer that provides softness, stretch, and pliability to the first material 200.

In one particular embodiment, the SMS laminate 146 can include a first spunbond layer 146A and a second spunbond layer 146C, where the spunbond layers 146A and 146C can be formed from any suitable polymer that provides softness, stretch, and pliability to the first material 200. For instance, the spunbond layers 146A and 146C can be formed from a semi-crystalline polyolefin. Exemplary polyolefins may include, for instance, polyethylene, polypropylene, blends and copolymers thereof. In one particular embodiment, a polyethylene is employed that is a copolymer of ethylene and an α-olefin, such as a $C_3$-$C_{20}$ α-olefin or $C_3$-$C_{12}$ α-olefin. Suitable α-olefins may be linear or branched (e.g., one or more $C_1$-$C_3$ alkyl branches, or an aryl group). Specific examples include 1-butene; 3-methyl-1-butene; 3,3-dimethyl-1-butene; 1-pentene; 1-pentene with one or more methyl, ethyl or propyl substituents; 1-hexene with one or more methyl, ethyl or propyl substituents; 1-heptene with one or more methyl, ethyl or propyl substituents; 1-octene with one or more methyl, ethyl or propyl substituents; 1-nonene with one or more methyl, ethyl or propyl substituents; ethyl, methyl or dimethyl-substituted 1-decene; 1-dodecene; and styrene. Particularly desired α-olefin co-monomers are 1-butene, 1-hexene and 1-octene. The ethylene content of such copolymers may be from about 60 mole % to about 99 mole %, in some embodiments from about 80 mole % to about 98.5 mole %, and in some embodiments, from about 87 mole % to about 97.5 mole %. The α-olefin content may likewise range from about 1 mole % to about 40 mole %, in some embodiments from about 1.5 mole % to about 15 mole %, and in some embodiments, from about 2.5 mole % to about 13 mole %.

The density of the polyethylene may vary depending on the type of polymer employed, but generally ranges from 0.85 to 0.96 grams per cubic centimeter ("g/cm$^3$"). Polyethylene "plastomers", for instance, may have a density in the range of from 0.85 to 0.91 g/cm$^3$. Likewise, "linear low density polyethylene" ("LLDPE") may have a density in the range of from 0.91 to 0.940 g/cm$^3$; "low density polyethylene" ("LDPE") may have a density in the range of from 0.910 to 0.940 g/cm$^3$; and "high density polyethylene" ("HDPE") may have density in the range of from 0.940 to 0.960 g/cm$^3$. Densities may be measured in accordance with ASTM 1505. Particularly suitable ethylene-based polymers for use in the present invention may be available under the designation EXACT™ from ExxonMobil Chemical Company of Houston, Tex. Other suitable polyethylene plastomers are available under the designation ENGAGE™ and AFFINITY™ from Dow Chemical Company of Midland, Mich. Still other suitable ethylene polymers are available from The Dow Chemical Company under the designations DOWLEX™ (LLDPE) and ATTANE™ (ULDPE). Other suitable ethylene polymers are described in U.S. Pat. No. 4,937,299 to Ewen et al.; U.S. Pat. No. 5,218,071 to Tsutsui et al.; U.S. Pat. No. 5,272,236 to Lai et at; and U.S. Pat. No. 5,278,272 to Lai et al., which are incorporated herein in their entirety by reference thereto for all purposes.

Of course, the spunbond layers 146A and 146C of the first material 200 are by no means limited to ethylene polymers. For instance, propylene polymers may also be suitable for use as a semi-crystalline polyolefin. Suitable propylene polymers may include, for instance, polypropylene homopolymers, as well as copolymers or terpolymers of propylene with an α-olefin (e.g., $C_3$-$C_{20}$) comonomer, such as ethylene, 1-butene, 2-butene, the various pentene isomers, 1-hexene, 1-octene, 1-nonene, 1-decene, 1-unidecene, 1-dodecene, 4-methyl-1-pentene, 4-methyl-1-hexene, 5-methyl-1-hexene, vinylcyclohexene, styrene, etc. The comonomer content of the propylene polymer may be about 35 wt. % or less, in some embodiments from about 1 wt. % to about 20 wt. %, in some embodiments, from about 2 wt. % to about 15 wt. %, and in some embodiments from about 3 wt. % to about 10 wt. %. The density of the polypropylene (e.g., propylene/α-olefin copolymer) may be 0.95 grams per cubic centimeter (g/cm$^3$) or less, in some embodiments, from 0.85 to 0.92 g/cm$^3$, and in some embodiments, from 0.85 g/cm$^3$ to 0.91 g/cm$^3$. In one particular embodiment, the spunbond layers 146A and 146C can each include a copolymer of polypropylene and polyethylene. The polypropylene can have a refractive index ranging from about 1.44 to about 1.54, such as from about 1.46 to about 1.52, such as from about 1.48 to about 1.50, such as about 1.49, while the polyethylene can have a refractive index ranging from about 1.46 to about 1.56, such as from about 1.48 to about 1.54, such as from about 1.50 to about 1.52, such as about 1.51, to impart the material 200 with the desired light scattering and light absorbing properties.

Suitable propylene polymers are commercially available under the designations VISTAMAXX™ from ExxonMobil Chemical Co. of Houston, Tex.; FINA™ (e.g., 8573) from Atofina Chemicals of Feluy, Belgium; TAFMER™ available from Mitsui Petrochemical Industries; and VERSIFY™ available from Dow Chemical Co. of Midland, Mich. Other examples of suitable propylene polymers are described in U.S. Pat. No. 6,500,563 to Datta et al.; U.S. Pat. No. 5,539,056 to Yang et al.; and U.S. Pat. No. 5,596,052 to Resconi et al., which are incorporated herein in their entirety by reference thereto for all purposes.

Any of a variety of known techniques may generally be employed to form the polyolefins. For instance, olefin polymers may be formed using a free radical or a coordination catalyst (e.g., Ziegler-Natta or metallocene). Metallocene-catalyzed polyolefins are described, for instance, in U.S. Pat. No. 5,571,619 to McAlpin et at; U.S. Pat. No. 5,322,728 to Davey et al.; U.S. Pat. No. 5,472,775 to Obijeski et al.; U.S. Pat. No. 5,272,236 to Lai et al.; and U.S. Pat. No. 6,090,325 to Wheat et al., which are incorporated herein in their entirety by reference thereto for all purposes.

The melt flow index (MI) of the polyolefins may generally vary, but is typically in the range of about 0.1 grams per 10 minutes to about 100 grams per 10 minutes, in some embodiments from about 0.5 grams per 10 minutes to about 30 grams per 10 minutes, and in some embodiments, about 1 to about 10 grams per 10 minutes, determined at 190° C. The melt flow index is the weight of the polymer (in grams) that may be forced through an extrusion rheometer orifice (0.0825-inch diameter) when subjected to a force of 2160 grams in 10 minutes at 190° C., and may be determined in accordance with ASTM Test Method D1238-E.

In addition to a polyolefin, the spunbond layers 146A and 146C can each include a slip additive to enhance the softness of the spunbond layers 146A and 146C. The slip additive can also reduce the glare of the first material 200 in the operating room by reducing the light reflectance of the first material and can also render the first material 200 more opaque than the standard gown material when contacted with fats and lipids during surgery, where the standard gown material turns transparent upon contact with fats and lipids, which can result in the wearer having some concern that the barrier properties of a standard gown have been compromised.

Variants of fatty acids can be used as slip additives. For example, the slip additive can be erucamide, oleamide, stearamide, behenamide, oleyl palmitamide, stearyl erucamide, ethylene bis-oleamide, N,N'-Ethylene Bis(Stearamide) (EBS), or a combination thereof. Further, the slip additive have a refractive index ranging from about 1.42 to about 1.52, such as from about 1.44 to about 1.50, such as from about 1.46 to about 1.48, such as about 1.47, to impart the material 200 with the desired light scattering and light absorbing properties by reducing the refractive index. The slip additive can be present in each of the first spunbond layer 146A and the second spunbond layer 146C in an amount ranging from about 0.25 wt. % to about 6 wt. %, such as from about 0.5 wt. % to about 5 wt. %, such as from about 1 wt. % to about 4 wt. % based on the total weight of the particular spunbond layer 146A or 146C. In one particular embodiment, the slip additive can be present in an amount of about 2 wt. % based on the total weight of the particular spunbond layer 146A or 146C.

In addition to the polyolefin and slip additive, the spunbond layers 146A and 146C can also include one or more pigments to help achieve the desired gray color of the gown 101. Examples of suitable pigments include, but are not limited to, titanium dioxide (e.g., SCC 11692 concentrated titanium dioxide), zeolites, kaolin, mica, carbon black, calcium oxide, magnesium oxide, aluminum hydroxide, and combinations thereof. In certain cases, for instance, each of the spunbond layers 146A or 146C can include titanium dioxide in an amount ranging from about 0.1 wt. % to about 10 wt. %, in some embodiments, from about 0.5 wt. % to about 7.5 wt. %, and in some embodiments, from about 1 wt. % to about 5 wt. % based on the total weight of the particular spunbond layer 146A or spunbond layer 146C. The titanium dioxide can have a refractive index ranging from about 2.2 to about 3.2, such as from about 2.4 to about 3, such as from about 2.6 to about 2.8, such as about 2.76, to impart the material 200 with the desired light scattering and light absorbing properties. Further, each of the spunbond layers 146A or 146C can also include carbon black in an amount ranging from about 0.1 wt. % to about 10 wt. %, in some embodiments, from about 0.5 wt. % to about 7.5 wt. %, and in some embodiments, from about 1 wt. % to about 5 wt. % based on the total weight of the particular spunbond layer 146A or spunbond layer 146C. The carbon black can have a refractive index ranging from about 1.2 to about 2.4, such as from about 1.4 to about 2.2, such as from about 1.6 to about 2 to impart the material 200 with the desired light scattering and light absorbing properties. In addition, each of the spunbond layers 146A or 146C can also include a blue pigment in an amount ranging from about 0.1 wt. % to about 10 wt. %, in some embodiments, from about 40.5 wt. % to about 7.5 wt. %, and in some embodiments, from about 1 wt. % to about 5 wt. % based on the total weight of the individual layer. The combination of the carbon black and blue pigment improves the ability of the spunbond layers 146A or 146C to absorb light.

The meltblown layer 146B of the spunbond-meltblown-spunbond second material 300 can also be formed from any of the semi-crystalline polyolefins discussed above with respect to the first spunbond layer 146A and the second spunbond layer 146C of the first material 200. In one particular embodiment, the meltblown layer 146B can be formed from 100% polypropylene.

Regardless of the specific polymer or polymers and additives used to form the SMS laminate 146, the SMS laminate 146 can have a basis weight ranging from about 5 gsm to about 50 gsm, such as from about 10 gsm to about 40 gsm, such as from about 15 gsm to about 30 gsm. In one particular embodiment, the SMS laminate 146 can have a basis weight of about 22 gsm (about 0.65 osy).

B. First and Second Rear Panels and Optional Second Portion of Hood

Despite the use of a front panel 102, sleeves 104, and hood 178 (e.g., all of the hood 178 or at least the first portion 256 of the hood 178 as described above) that are formed from an air impermeable but moisture-vapor breathable first material 200, the amount of heat that becomes trapped can be uncomfortable to the wearer.

As such, the present inventor has discovered that the placement of a highly breathable and air permeable first rear panel 120 and second rear panel 120 formed from a second material 300 in the rear 160 of the gown 101 can facilitate the dissipation of trapped humidity and heat between the gown 101 and the wearer. Further, in some embodiments, a second portion 258 of the hood 178 below seam 254 at the rear 160 of the gown 101 can optionally be formed from the second material 300.

In one particular embodiment, the second material 300 can be in the form of a spunbond-meltblown-spunbond (SMS) laminate that has enhanced air breathability in order to facilitate removal of trapped heated air and moisture from the gown 101. For instance, the second material 300 allows for an air volumetric flow rate ranging from about 20 standard cubic feet per minute (scfm) to about 80 scfm, such as from about 30 scfm to about 70 scfm, such as from about 40 scfm to about 60 scfm, as determined at 1 atm (14.7 psi) and 20° C. (68° F.). In one particular embodiment, the second material 300 allows for an air volumetric flow rate of about 45 scfm. Because the first rear panel 120, the second rear panel 122, and lower or second portion 256 of the hood 178 below seam 254 at the rear 160 of the gown 101 can be formed from the air breathable second material 300, the heat and humidity that can build up inside the space between the gown 101 and the wearer's body can escape via convection and/or by movement of air as the movement of the gown materials 200 and 300 changes the volume of space between the gown 101 and the wearer's body. Further, the SMS laminate used to form the second material 300 can have a basis weight ranging from about 20 gsm to about 80 gsm, such as from about 25 gsm to about 70 gsm, such as from about 30 gsm to about 60 gsm. In one particular embodiment, the second material 300 can have a basis weight of about 40 gsm (about 1.2 osy).

The various layers of the second material 300 are discussed in more detail below.

i. First and Second Spunbond Layers

The first spunbond layer 148 and second spunbond layer 152 of the second material 300 can be formed from any suitable polymer that provides softness and air breathability to the second material 300. For instance, the first spunbond layer 148 and the second spunbond layer 152 can be formed from a semi-crystalline polyolefin. Exemplary polyolefins may include, for instance, polyethylene, polypropylene, blends and copolymers thereof. In one particular embodiment, a polyethylene is employed that is a copolymer of ethylene and an α-olefin, such as a $C_3$-$C_{20}$ α-olefin or $C_3$-$C_{12}$ α-olefin. Suitable α-olefins may be linear or branched (e.g., one or more $C_1$-$C_3$ alkyl branches, or an aryl group). Specific examples include 1-butene; 3-methyl-1-butene; 3,3-dimethyl-1-butene; 1-pentene; 1-pentene with one or more methyl, ethyl or propyl substituents; 1-hexene with one or more methyl, ethyl or propyl substituents; 1-heptene with one or more methyl, ethyl or propyl substituents; 1-octene with one or more methyl, ethyl or propyl substituents; 1-nonene with one or more methyl, ethyl or propyl substituents; ethyl, methyl or dimethyl-substituted 1-decene; 1-dodecene; and styrene. Particularly desired α-olefin co-monomers are 1-butene, 1-hexene and 1-octene. The ethylene content of such copolymers may be from about 60 mole % to about 99 mole %, in some embodiments from about 80 mole % to about 98.5 mole %, and in some embodiments, from about 87 mole % to about 97.5 mole %. The α-olefin content may likewise range from about 1 mole % to about 40 mole %, in some embodiments from about 1.5 mole % to about 15 mole %, and in some embodiments, from about 2.5 mole % to about 13 mole %.

The density of the polyethylene may vary depending on the type of polymer employed, but generally ranges from 0.85 to 0.96 grams per cubic centimeter ("$g/cm^3$"). Polyethylene "plastomers", for instance, may have a density in the range of from 0.85 to 0.91 $g/cm^3$. Likewise, "linear low density polyethylene" ("LLDPE") may have a density in the range of from 0.91 to 0.940 $g/cm^3$; "low density polyethylene" ("LDPE") may have a density in the range of from 0.910 to 0.940 $g/cm^3$; and "high density polyethylene" ("HDPE") may have density in the range of from 0.940 to 0.960 $g/cm^3$. Densities may be measured in accordance with ASTM 1505. Particularly suitable ethylene-based polymers for use in the present invention may be available under the designation EXACT™ from ExxonMobil Chemical Company of Houston, Tex. Other suitable polyethylene plastomers are available under the designation ENGAGE™ and AFFINITY™ from Dow Chemical Company of Midland, Mich. Still other suitable ethylene polymers are available from The Dow Chemical Company under the designations DOWLEX™ (LLDPE) and ATTANE™ (ULDPE). Other suitable ethylene polymers are described in U.S. Pat. No. 4,937,299 to Ewen et al.; U.S. Pat. No. 5,218,071 to Tsutsui et al.; U.S. Pat. No. 5,272,236 to Lai et at; and U.S. Pat. No. 5,278,272 to Lai et al., which are incorporated herein in their entirety by reference thereto for all purposes.

Of course, the first spunbond layer 148 and the second spunbond layer 152 of the second material 300 are by no means limited to ethylene polymers. For instance, propylene polymers may also be suitable for use as a semi-crystalline polyolefin. Suitable propylene polymers may include, for instance, polypropylene homopolymers, as well as copolymers or terpolymers of propylene with an α-olefin (e.g., $C_3$-$C_{20}$) comonomer, such as ethylene, 1-butene, 2-butene, the various pentene isomers, 1-hexene, 1-octene, 1-nonene, 1-decene, 1-unidecene, 1-dodecene, 4-methyl-1-pentene, 4-methyl-1-hexene, 5-methyl-1-hexene, vinylcyclohexene, styrene, etc. The comonomer content of the propylene polymer may be about 35 wt. % or less, in some embodiments from about 1 wt. % to about 20 wt. %, in some embodiments, from about 2 wt. % to about 15 wt. %, and in some embodiments from about 3 wt. % to about 10 wt. %. The density of the polypropylene (e.g., propylene/α-olefin copolymer) may be 0.95 grams per cubic centimeter (g/cm$^3$) or less, in some embodiments, from 0.85 to 0.92 g/cm$^3$, and in some embodiments, from 0.85 g/cm$^3$ to 0.91 g/cm$^3$. In one particular embodiment, the spunbond layers 148 and 152 can each include a copolymer of polypropylene and polyethylene. The polypropylene can have a refractive index ranging from about 1.44 to about 1.54, such as from about 1.46 to about 1.52, such as from about 1.48 to about 1.50, such as about 1.49, while the polyethylene can have a refractive index ranging from about 1.46 to about 1.56, such as from about 1.48 to about 1.54, such as from about 1.50 to about 1.52, such as about 1.51, to impart the material 300 with the desired light scattering and light absorbing properties.

Suitable propylene polymers are commercially available under the designations VISTAMAXX™ from ExxonMobil Chemical Co. of Houston, Tex.; FINA™ (e.g., 8573) from Atofina Chemicals of Feluy, Belgium; TAFMER™ available from Mitsui Petrochemical Industries; and VERSIFY™ available from Dow Chemical Co. of Midland, Mich. Other examples of suitable propylene polymers are described in U.S. Pat. No. 6,500,563 to Datta et al.; U.S. Pat. No. 5,539,056 to Yang et al.; and U.S. Pat. No. 5,596,052 to Resconi et al., which are incorporated herein in their entirety by reference thereto for all purposes.

Any of a variety of known techniques may generally be employed to form the polyolefins. For instance, olefin polymers may be formed using a free radical or a coordination catalyst (e.g., Ziegler-Natta or metallocene). Metallocene-catalyzed polyolefins are described, for instance, in U.S. Pat. No. 5,571,619 to McAlpin et al.; U.S. Pat. No. 5,322,728 to Davey et al.; U.S. Pat. No. 5,472,775 to Obijeski et al.; U.S. Pat. No. 5,272,236 to Lai et al.; and U.S. Pat. No. 6,090,325 to Wheat et al., which are incorporated herein in their entirety by reference thereto for all purposes.

The melt flow index (MI) of the polyolefins may generally vary, but is typically in the range of about 0.1 grams per 10 minutes to about 100 grams per 10 minutes, in some embodiments from about 0.5 grams per 10 minutes to about 30 grams per 10 minutes, and in some embodiments, about 1 to about 10 grams per 10 minutes, determined at 190° C. The melt flow index is the weight of the polymer (in grams) that may be forced through an extrusion rheometer orifice (0.0825-inch diameter) when subjected to a force of 2160 grams in 10 minutes at 190° C., and may be determined in accordance with ASTM Test Method D1238-E.

In addition to a polyolefin, the first spunbond layer 148 and the second spunbond layer 152 can also include a slip additive to enhance the softness of the first spunbond layer 148 and the second spunbond layer 152. The slip additive can also reduce the coefficient of friction and increase the hydrohead of the first spunbond layer 148 and the second spunbond layer 152 of the first rear panel 120 and second rear panel 122. Such a reduction in the coefficient of friction lessens the chance of the gown 101 being cut or damaged due to abrasions and also prevents fluids from seeping through the second material 300. Instead, at least in part due to the inclusion of the slip additive, fluid that contacts the outer-facing surface 302 of the gown 101 can remain in droplet form and run vertically to the distal end 156 of the gown 101 and onto the floor. The slip additive can also reduce the glare of the second material 300 in the operating room by reducing the light reflectance of the first material and can also render the second material 300 more opaque than the standard gown material when contacted with fats and lipids during surgery, where the standard gown material turns transparent upon contact with fats and lipids, which can result in the wearer having some concern that the barrier properties of a standard gown have been compromised.

The slip additive can function by migrating to the surface of the polymer used to form the first spunbond layer 148 and/or the second spunbond layer 152, where it can provide a coating that reduces the coefficient of friction of the outer-facing surface 302 and/or body-facing surface or inner-facing surface 304 of the first material 300. Variants of fatty acids can be used as slip additives. For example, the slip additive can be erucamide, oleamide, stearamide, behenamide, oleyl palmitamide, stearyl erucamide, ethylene bisoleamide, N,N'-Ethylene Bis(Stearamide) (EBS), or a combination thereof. Further, the slip additive can have a refractive index ranging from about 1.42 to about 1.52, such as from about 1.44 to about 1.50, such as from about 1.46 to about 1.48, such as about 1.47, to impart the material 200 with the desired light scattering and light absorbing properties. The slip additive can be present in the first spunbond layer 148 and/or the second spunbond layer 152 of the second material 300 in an amount ranging from about 0.25 wt. % to about 6 wt. %, such as from about 0.5 wt. % to about 5 wt. %, such as from about 1 wt. % to about 4 wt. % based on the total weight of the first spunbond layer 148 and/or the second spunbond layer 152. In one particular embodiment, the slip additive can be present in an amount of about 2 wt. % based on the total weight of the first spunbond layer 148 and/or the second spunbond layer 152.

In addition to the polyolefin and slip additive, the spunbond layers 148 and 152 can also include one or more pigments to help achieve the desired gray color of the gown 101. Examples of suitable pigments include, but are not limited to, titanium dioxide (e.g., SCC 11692 concentrated titanium dioxide), zeolites, kaolin, mica, carbon black, calcium oxide, magnesium oxide, aluminum hydroxide, and combinations thereof. In certain cases, for instance, each of the spunbond layers 148 or 152 can include titanium dioxide in an amount ranging from about 0.1 wt. % to about 10 wt.

%, in some embodiments, from about 0.5 wt. % to about 7.5 wt. %, and in some embodiments, from about 1 wt. % to about 5 wt. % based on the total weight of the particular spunbond layer 148 or 152. The titanium dioxide can have a refractive index ranging from about 2.2 to about 3.2, such as from about 2.4 to about 3, such as from about 2.6 to about 2.8, such as about 2.76, to impart the material 200 with the desired light scattering and light absorbing properties. Further, each of the spunbond layers 148 or 152 can also include carbon black in an amount ranging from about 0.1 wt. % to about 10 wt. %, in some embodiments, from about 0.5 wt. % to about 7.5 wt. %, and in some embodiments, from about 1 wt. % to about 5 wt. % based on the total weight of the particular spunbond layer 148 or spunbond layer 152. The carbon black can have a refractive index ranging from about 1.2 to about 2.4, such as from about 1.4 to about 2.2, such as from about 1.6 to about 2 to impart the material 300 with the desired light scattering and light absorbing properties. In addition, each of the spunbond layers 148 or 152 can also include a blue pigment in an amount ranging from about 0.1 wt. % to about 10 wt. %, in some embodiments, from about 0.5 wt. % to about 7.5 wt. %, and in some embodiments, from about 1 wt. % to about 5 wt. % based on the total weight of the individual layer. The combination of the carbon black and blue pigment improves the ability of the spunbond layers 148 or 152 to absorb light.

ii. Meltblown Layer

The meltblown layer 150 of the spunbond-meltblown-spunbond second material 300 can also be formed from any of the semi-crystalline polyolefins discussed above with respect to the first spunbond layer 148 and the second spunbond layer 152 of the second material 300. In one particular embodiment, the meltblown layer 150 can be formed from 100% polypropylene.

C. Cuffs and Collar

The cuffs 106 and collar 110 (if present) of the disposable surgical gown 101 of the present invention can be formed from a woven or knit material that is air breathable, soft, and extensible. The collar 110 can also be water repellant. In one particular embodiment, the collar 110 and the cuffs 104 can be formed from a knit polyester. Because the material from which the collar 110 is formed is extensible, the collar 110 can stretch and conform to a wearer's particular neck dimensions to lay flat against the wearer's neck and prevent any gapping of the collar 110, which could allow bone fragments, blood splatter, and other biologic materials to come into contact with the wearer. In any event, the collar 110 can be sewn to the front panel 102, sleeves 104, first rear panel 120, and second rear panel 122 with a polyester thread. Further, the cuffs 106 can be formed from the same material as the collar 110, as discussed above. In addition, the cuffs 106 can be sewn to the sleeves 104 with a polyester thread.

III. Donning of the Personal Protection and Ventilation System

Now that the various non-sterile and sterile components of the personal protection and ventilation system have been described in detail, the manner in which the various components can be donned will be discussed. Generally, when the personal protection and ventilation system 100 is completely donned, the user or wearer's head is completely contained within the hood 178, while the visor 180 provides visibility in the form of a clear shield, and the optional light source 188 on the helmet 190 provides illumination during a surgical procedure (see FIG. 18C). Further, the hood 178 is connected to the helmet 190 via connecting tabs 210 present on the first side 266 and the second side 268 of the visor 180 and located inside the hood 178, where the connecting tabs 210 mate or lock with the receiving tabs 208 on either side of the helmet 190 (see FIGS. 1-3 and 17A-17C).

Figure 16:
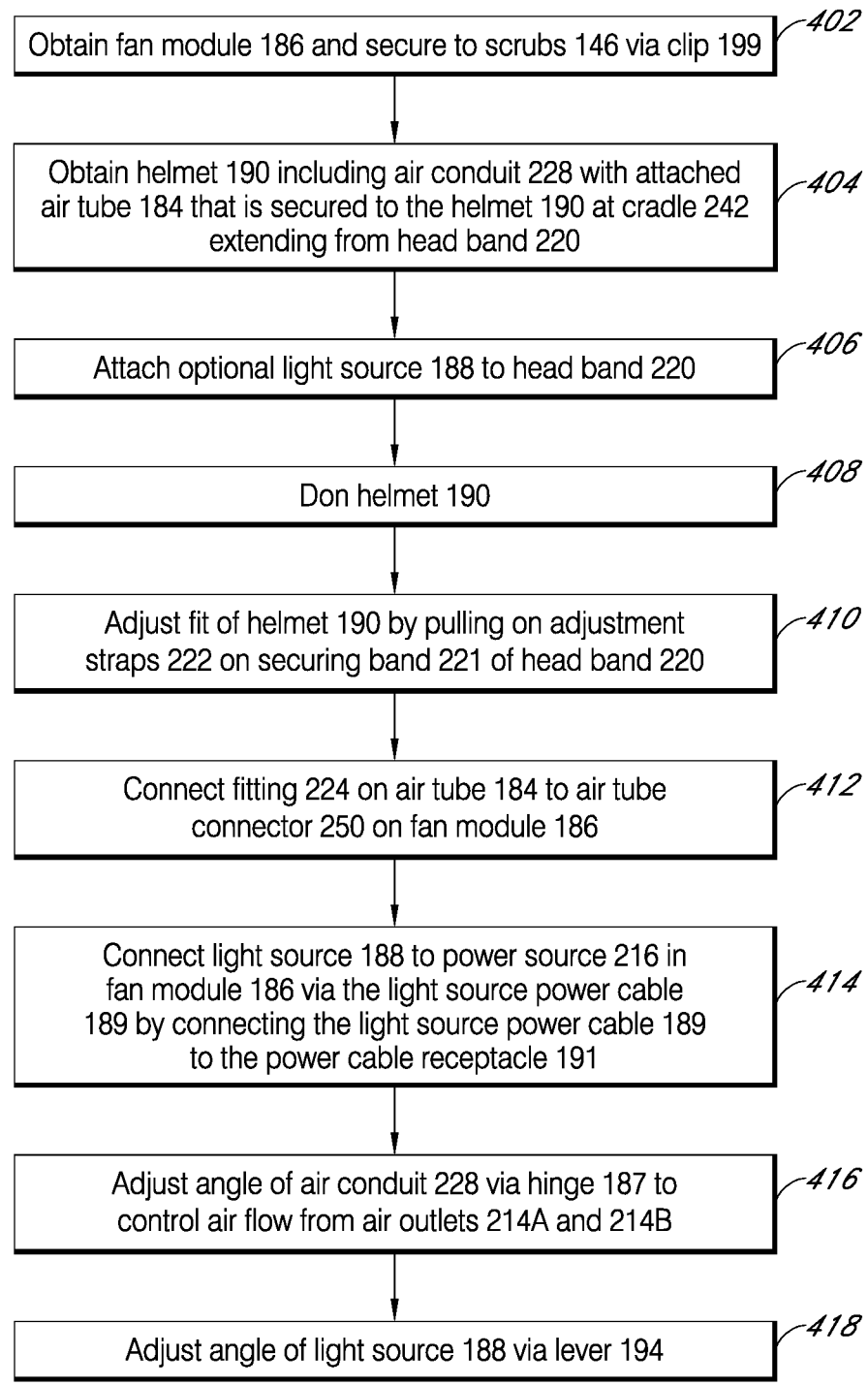
FIG. 16 illustrates a flow chart of a procedure for donning the non-sterile components (e.g., the helmet with optional light source, the air tube, and the fan component or module) of a personal protection and ventilation system contemplated by the present invention.

Referring to FIGS. 16-18D, the procedures for donning and use of the personal protection and ventilation system 100 are described in more detail. FIG. 16 illustrates a procedure for donning the non-sterile components (e.g., the helmet 190 with optional light 188, the air tube 184, and the fan component or module 186 of a personal protection and ventilation system 100 contemplated by the present invention; FIGS. 17A-17F illustrate a procedure for donning the disposable surgical gown 101 and hood 178 of a personal protection and ventilation system 100 contemplated by the present invention; and FIGS. 18A-18D illustrates various adjustment procedures that can be carried out while using the personal protection and ventilation system 100 contemplated by the present invention.

Turning now to FIG. 16, the procedure 400 that may be followed to don the non-sterile components (e.g., the helmet 190, the air tube 184, the fan module 186, and the optional light source 188) will be described in detail. First, in step 402, a healthcare professional or other user of the personal protection and ventilation system 100 can obtain a fan module 186, such as from a fan module charging unit 270, and attach the fan module 186 about a side or rear portion of the waist of his or her scrubs 246 via a clip 199 on the fan module 186 (see FIG. 17A). Next, in step 404, the user can obtain a helmet 190 with an air conduit 228 that has an air tube 184 secured to the helmet 190 at cradle 242, where the cradle extends from a head band 220. Then, in step 406, the user can attach an optional light source 188 to the head band 220, such as at hinged connection point 196. Next, in step 408, the user can don then helmet, while in step 410, the user can adjust the fit of the helmet 190 by pulling on adjustment straps 222 on the securing band 221 of the head band 220. Then, in step 412, the user can connect the fitting 224 on the air tube 184 to the air tube connector 250 on the fan module 186. Further, in step 414, the user can connect the light source 188 to the power source 216 in the fan module 186 via the light source power cable 189 by connecting the light source power cable 189 to the power cable receptacle 191 present on the fan module 186. Next, in step 416, the angle of the air conduit 228 can be adjusted via the hinge 187 to control the air flow from the air outlets 214A and 214B. Then, the angle of the optional light source 188 can be adjusted via lever 194 as facilitated by the hinged connection point 196.

After the user or wearer has donned the non-sterile components of the personal protection and ventilation system 100 (e.g., the helmet 190, fan component or module 186, air tube 184, and optional light source 188 as described above), the user or wearer can then don the surgical gown 101 of the personal protection and ventilation system 100 of the present invention, as shown in FIGS. 17A-17F. The gown 101 can include an integral or separate hood 178 and visor 180 (see FIGS. 3-4, and 10-13). In any event, as previously described, the visor 180 component of the hood 178 can include connecting tabs 210 for securing the hood 178 to the helmet 190, as illustrated in FIG. 3, where only the visor 180 portion of the surgical gown 101 is depicted to clearly show the connection mechanism between tabs 208 and 210. Specifically, the visor 180 can be positioned adjacent the front portion 232 of the helmet 190 near the air outlets 214A and 214B located at the end of the air conduit 228 of the helmet 190. The visor 180 can include connecting tabs 210 on opposing sides 266 and 268 of the visor 180, where the connecting tabs correspond with receiving tabs 208 on the first side 238 and second side 240 of the helmet 190 (see FIGS. 17A-17C and 18). The tabs 210 can lock into place with a clicking sound or other suitable haptic feedback to indicate that the tabs 210 on the visor 180 have been securely mated with the receiving tabs 208 on the helmet 190.

Once the tabs 208 and 210 have been locked into place with each other as described above so that the hood 178 is securely attached to the user or wearer's helmet 190, another medical professional can secure the surgical gown 101 with hood 178 of the personal protection and ventilation system 100 of the present via the rear fastening means 118 (e.g., a zipper). As shown, the fan component or module 186 is located outside the wearer's scrubs 246 so that the fan 182 can draw air in from the outside atmosphere once the surgical gown 101 is completely secured via the rear panels 120 and 122, which are formed from a nonwoven laminate that is air breathable and allows for an air volumetric flow rate ranging from about 20 standard cubic feet per minute (scfm) to about 80 scfm as described in detail above. Therefore, the fan 182 is able to intake a sufficient amount of air from the environment through the rear panels 120 and 122 in order to provide cooling and ventilation inside the secured hood 178.

Figure 17B:
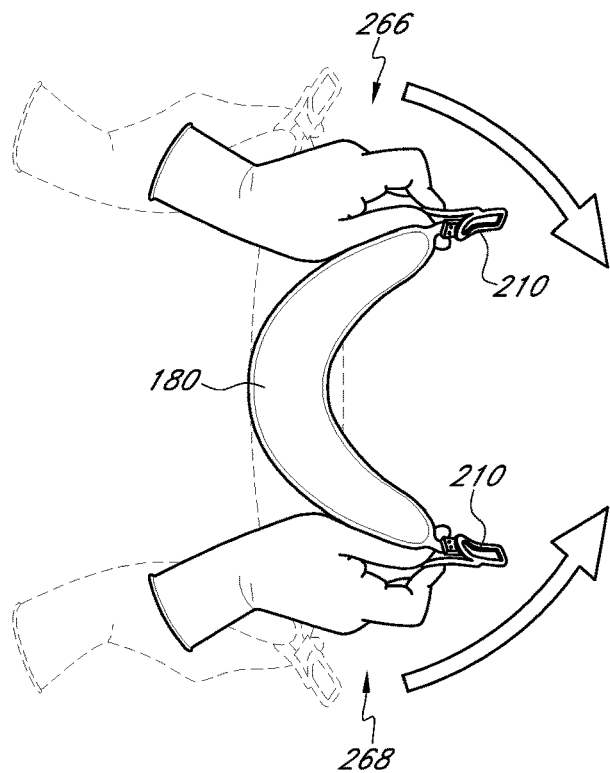
Figure 17C:
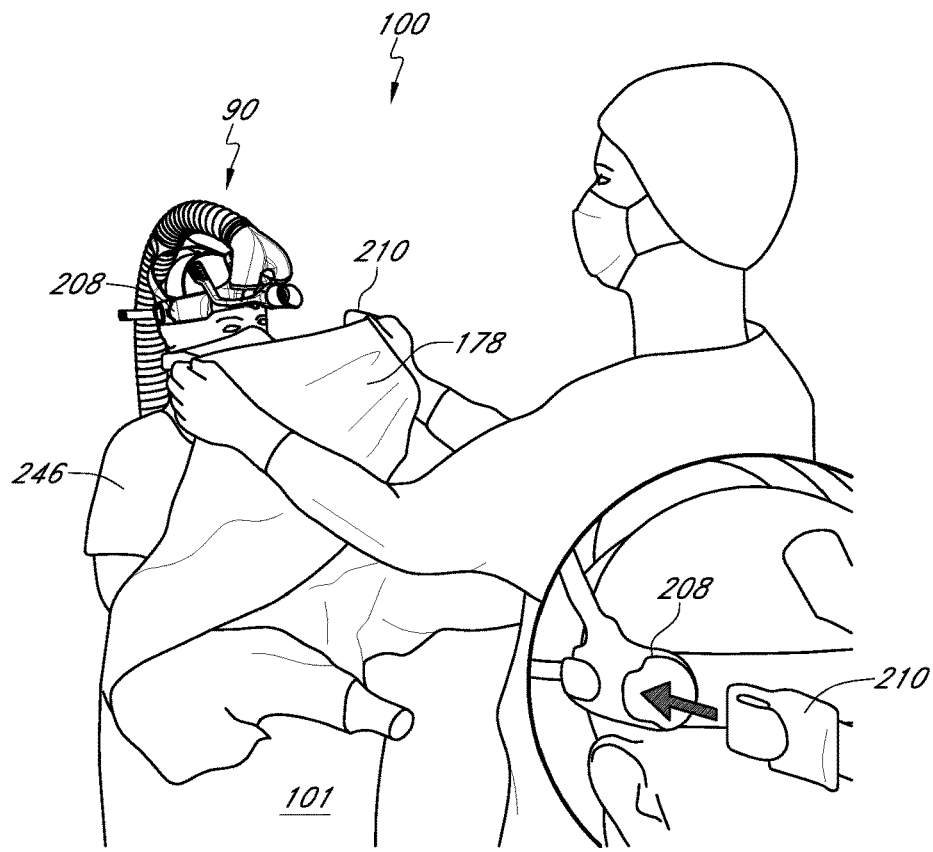
Figure 17D:
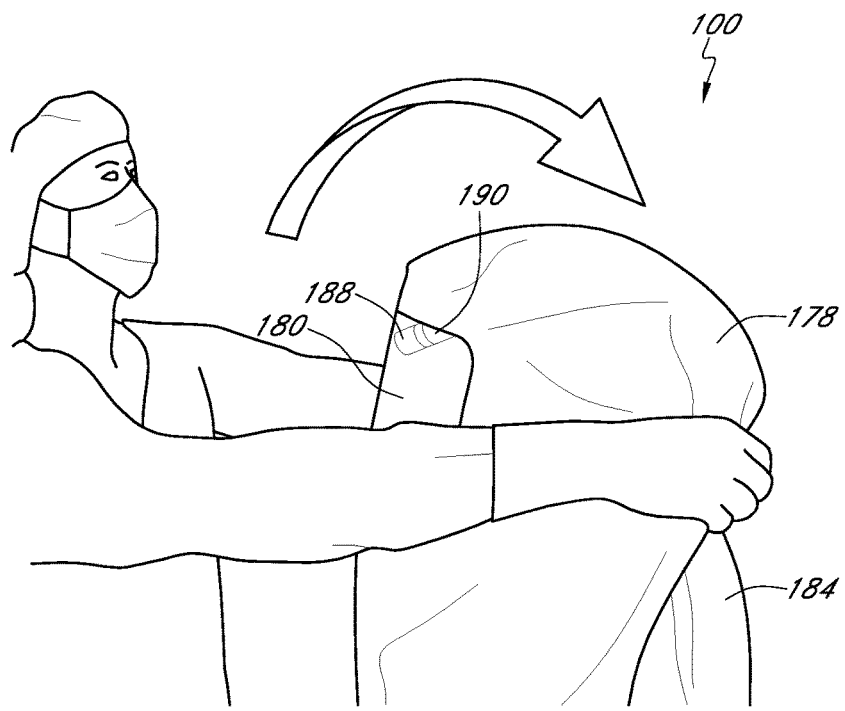
Figure 17E:
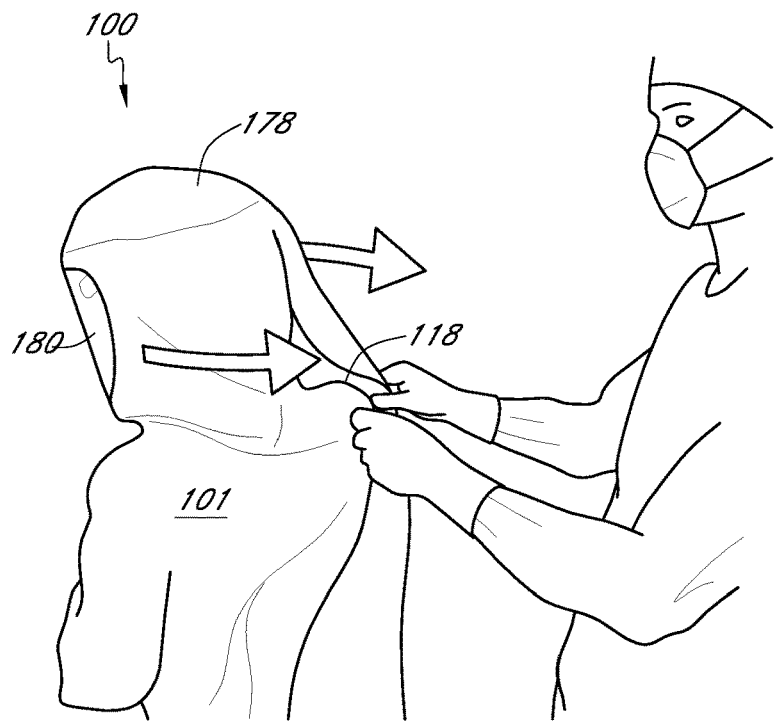
Figure 17F:
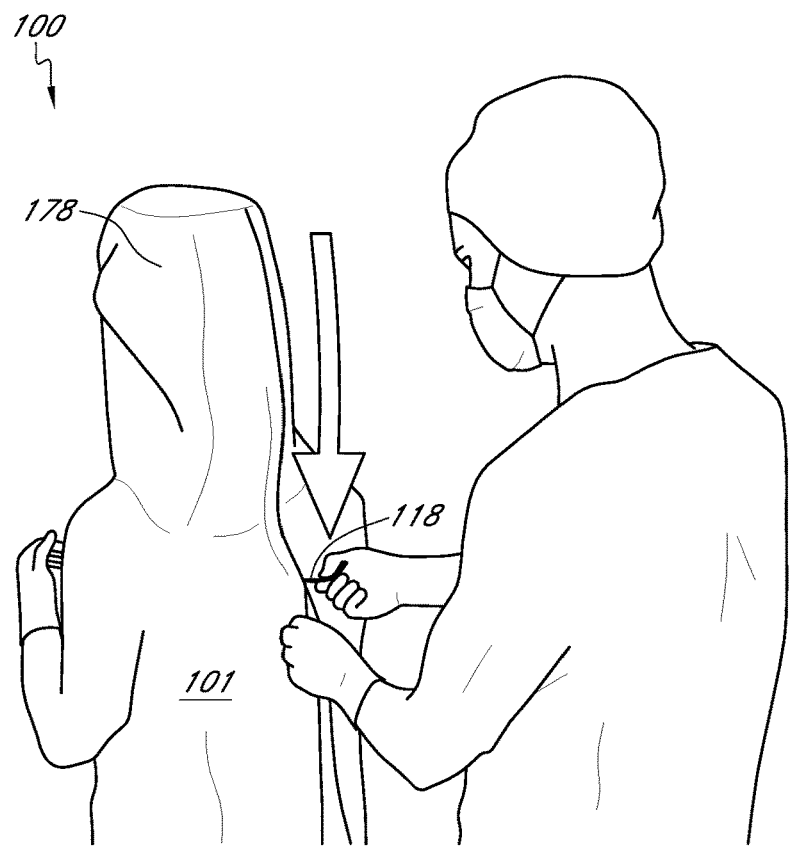

Specifically, FIGS. 17A-17F illustrate a procedure by which a wearer can don the disposable surgical gown 101 with hood 178 and visor 180 after donning the helmet 190, air tube 184, and fan component or module 186 of the personal ventilation and protection system 100 of the present invention as described above in FIG. 16 is shown. First, with an assistant, the wearer can insert his arms into the sleeves of the gown 101 as shown in FIG. 17A. Then, as shown in FIG. 17B, the assistant can bend the connecting tabs 210 on the visor 180 towards each other in the direction of the arrows as shown from the outside of the hood 178, and, next, as shown in FIG. 17C, the assistant can move the hood 178 in the direction of the wearer to line up the connecting tabs 210 on the visor 180 on the hood 178 with the receiving tabs 210 on the helmet 190. Further, as the visor 180 is connected to the helmet 190, as shown in FIG. 17D, the assistant can position the hood 178 over the helmet 190 and the air tube 184. Then, as shown in FIG. 17E, the assistant can ensure that the hood 178 and gown 101 are properly donned and positioned about the body of the wearer, and lastly, as shown in FIG. 17F, the assistant can secure the gown 101 via fastening means 118 (e.g., a zipper) by pulling the zipper downward as shown.

Figure 18A:
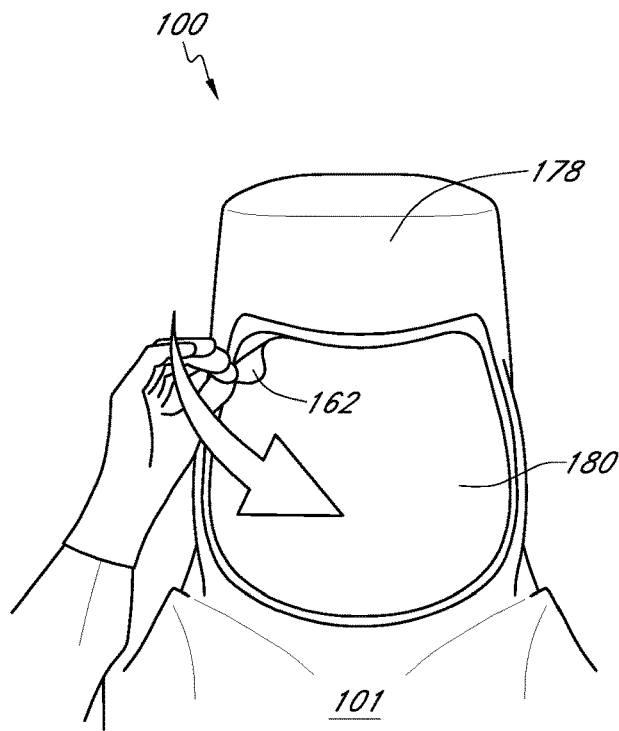
FIGS. 18A, 18B, 18C, and 18D illustrate various adjustment procedures that can be carried out while using the personal protection and ventilation system contemplated by the present invention.
Figure 18B:
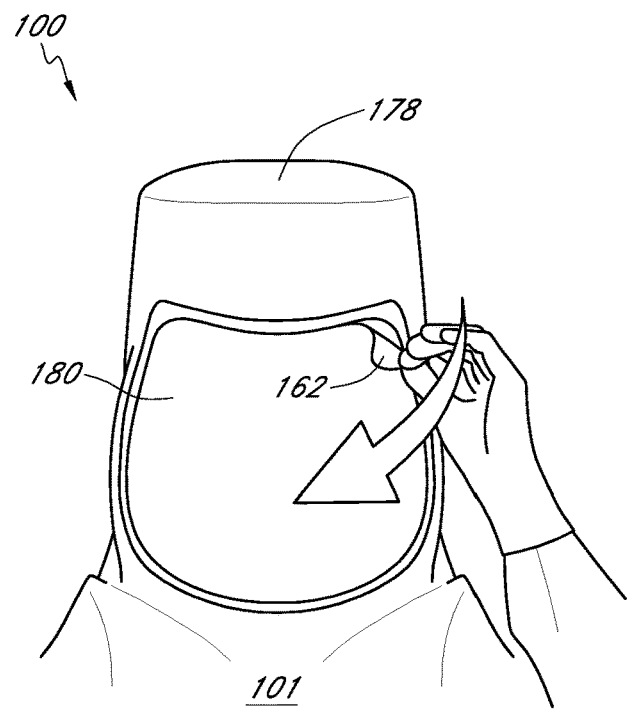
Figure 18C:
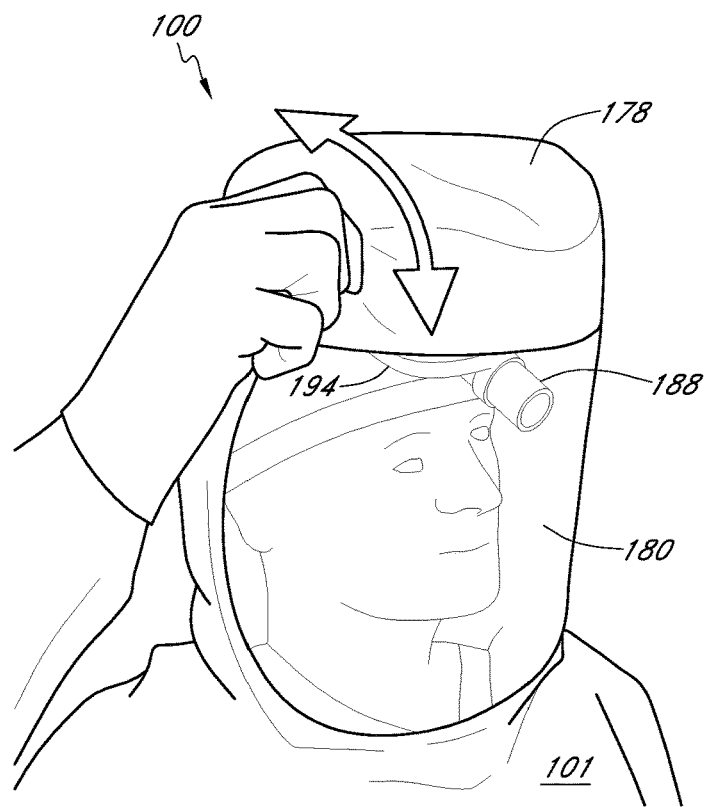
Figure 18D:
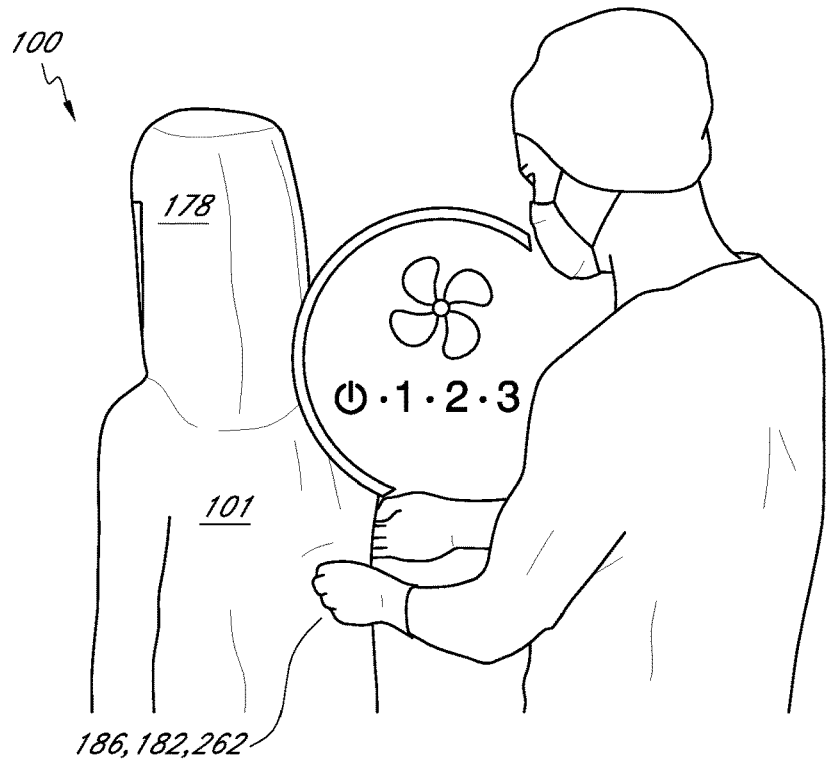

Further, in FIGS. 18A-18D, various adjustment procedures that can be carried out while using the personal protection and ventilation system 100 contemplated by the present invention are shown. In FIGS. 18A and 18B, the removal of a clear film 162 disposed on the visor 180 of the hood 178 is shown. Removal of the film 162 may be desired when blood, tissue, etc. are present on the film 162 and affect the wearer's visibility during a surgical procedure. In FIG. 18C, adjustment of the positioning of the light source 188 is shown by the wearer grasping the lever 194, where the hood 178 is present between the wearer's fingers and the lever 194 contained within the hood 178. Lastly, in FIG. 18D, adjustment of the speed of the fan 182 by an assistant is shown, where the fan 182 can be adjusted to various speeds (e.g., low, medium, and high) via button 262 either by unfastening (e.g., unzipping) the gown 101 via fastening means 118 (see FIG. 22, step 6), or tactically through the gown 101 without unfastening the gown 101.

The present invention may be better understood with reference to the following examples.

Example 1

In Example 1, the opacity (diffuse reflectance), scattering power, scattering coefficient, absorption power, absorption coefficient, and transmittance were determined for the elastic film nonwoven laminate of the present invention according to a standard TAPPI test method for paper using C-illuminant as the light source, which is similar to light sources used in hospital operating rooms. The same properties were also determined for three commercially available materials used in disposable surgical gowns. The basis weight for the materials was also determined. The results are summarized in Table 1 below:

TABLE 1

Gown Material Properties

| Test | Material of Present Invention | Microcool | Aero Blue | Prevention Plus | SmartGown |
|---|---|---|---|---|---|
| Opacity (Diffuse Reflectance Using C-illuminant) (%) | 99.2 | 97.9 | 97.3 | 89.7 | 87.1 |
| Scattering Power | 2.16 | 2.74 | 1.34 | 0.701 | 1.12 |
| Scattering Coefficient ($m^2/g$) | 32.0 | 41.3 | 24.0 | 11.5 | 16.2 |
| Absorption Power | 1.05 | 0.515 | 0.869 | 0.603 | 0.327 |
| Absorption Coefficient ($m^2/g$) | 15.5 | 7.77 | 15.6 | 9.89 | 4.71 |
| Transmittance | 0.081 | 0.124 | 0.157 | 0.326 | 0.344 |
| Basis Weight (gsm) | 67.5 | 66.3 | 55.8 | 61.0 | 69.4 |

As shown above, the material used in the disposable surgical gown component of the personal protection and ventilation system of the present invention has a lower transmittance and higher opacity than the other four materials tested.

Example 2

In Example 2, a user or wearer donned the personal protection and ventilation system of the present invention, along with two comparative systems that are commercially available. Then, with the fans in each system operating at a low speed setting and the high speed setting, auditory testing was conducted to determine the decibel level at which a person near the user or wearer had to speak in order for the user or wearer to hear 50%, 80%, and 90% of the words spoken by the person. The results are shown in Table 2 below.

TABLE 2

Auditory Testing of the Personal Protection and Ventilation System of the Present Invention Compared to Commercially Available Personal Protection and Ventilation Systems

| System | Speed | Specified Probability (% of Words Heard) | Decibel Level | Lower 95% | Upper 95% |
|---|---|---|---|---|---|
| Comparative 1 | Low | 50 | 47.34 | 41.24 | 53.41 |
| Comparative 1 | Low | 80 | 55.66 | 49.74 | 62.61 |
| Comparative 1 | Low | 90 | 60.53 | 54.40 | 68.30 |
| Comparative 1 | High | 50 | 73.60 | 67.54 | 79.70 |
| Comparative 1 | High | 80 | 81.92 | 75.99 | 88.96 |
| Comparative 1 | High | 90 | 86.79 | 80.62 | 94.67 |
| Comparative 2 | Low | 50 | 45.27 | 39.15 | 51.32 |
| Comparative 2 | Low | 80 | 53.59 | 47.67 | 60.49 |
| Comparative 2 | Low | 90 | 58.45 | 52.34 | 66.18 |
| Comparative 2 | High | 50 | 52.85 | 46.72 | 58.96 |
| Comparative 2 | High | 80 | 61.17 | 55.22 | 68.16 |
| Comparative 2 | High | 90 | 66.04 | 59.88 | 73.85 |
| Present Invention | Low | 50 | 16.97 | 3.44 | 28.64 |
| Present Invention | Low | 80 | 25.29 | 12.76 | 37.02 |
| Present Invention | Low | 90 | 30.16 | 18.04 | 42.09 |
| Present Invention | High | 50 | 28.18 | 20.78 | 34.95 |
| Present Invention | High | 80 | 36.50 | 29.70 | 43.73 |
| Present Invention | High | 90 | 41.37 | 34.61 | 49.16 |

As shown above, the personal protection and ventilation system of the present invention allowed for the user or wearer to hear words spoken by others at much lower decibels levels compared to the two commercially available personal protection and ventilation systems. In other words, at low and high fan speeds, people in the vicinity of the user or wearer did not have to speak as loudly in order for the user or wearer to hear what the other people were saying when the user or wearer donned the personal protection and ventilation system of the present invention compared to two commercially available systems.

The present invention has been described both in general and in detail by way of examples. These and other modifications and variations of the present invention may be practiced by those of ordinary skill in the art, without departing from the spirit and scope of the present invention. In addition, it should be understood that aspects of the various embodiments may be interchanged both in whole or in part. Furthermore, those of ordinary skill in the art will appreciate that the foregoing description is by way of example only, and is not intended to limit the invention so further described in such appended claims.

What is claimed is:

1. A personal protection and ventilation system comprising:
    a disposable surgical gown comprising a front panel, a first sleeve, a second sleeve, a rear panel, a hood, and a visor, wherein the front panel, the first sleeve, the second sleeve, and at least a part of the hood are formed from a first material comprising an outer spunbond layer having a surface that defines an outer-facing surface of the disposable surgical gown, a spunbond-meltblown-spunbond (SMS) laminate having a surface that defines a body-facing surface of the disposable surgical gown, and a liquid impervious elastic film disposed therebetween, wherein the elastic film meets the requirements of ASTM-1671, wherein the first material has an air volumetric flow rate of less than 1 standard cubic feet per minute (scfm), and wherein the rear panel is formed from a second material comprising a nonwoven laminate that is air breathable, wherein the second material has an air volumetric flow rate ranging from 20 scfm to 80 scfm;
    a helmet having a first side and a second side, an air conduit extending from a rear portion of the helmet to a front portion of the helmet to define a bifurcated air outlet, and a head band having a front portion and a rear portion, wherein the rear portion of the head band includes a cradle;
    a fan module comprising a fan, wherein the fan intakes air from an outside environment through the rear panel of the disposable surgical gown, wherein the fan is positioned between the wearer and an inner-facing surface of the rear panel of the disposable surgical gown; and
    an air tube, wherein the air tube delivers air taken in from the fan module to the helmet, wherein the cradle engages with the air tube, wherein the air conduit then delivers the air to the bifurcated air outlet at the front portion of the helmet to provide ventilation to the wearer.

2. The personal protection and ventilation system of claim 1, wherein the bifurcated air outlet is positioned at an angle $\alpha$ that ranges from 5° to 60° with respect to an x-axis or horizontal direction towards a y-axis or vertical direction.

3. The personal protection and ventilation system of claim 1, wherein the air conduit and the head band are formed from a polymer, cellulose, or a combination thereof.

4. The personal protection and ventilation system of claim 1, wherein the hood is formed completely from the first material.

5. The personal protection and ventilation system of claim 1, wherein a first portion of the hood is formed from the first material and a second portion of the hood is formed from the second material, wherein the first portion and the second portion are separated by a seam located at a rear of the disposable surgical gown, wherein the first portion is located above the seam and includes all of the hood above the seam, and wherein the second portion is located below the seam.

6. The personal protection and ventilation system of claim 1, wherein the visor includes a first connecting tab present on a first side of the visor and a second connecting tab present on a second side of the visor, wherein the helmet includes a first receiving tab on the first side of the helmet and a second receiving tab present on the second side of the helmet, wherein the first and second connecting tabs and the first and second receiving tabs secure the disposable surgical gown to the helmet when engaged.

7. The personal protection and ventilation system of claim 1, wherein the head band includes padding disposed between the front portion of the head band and the wearer.

8. The personal protection and ventilation system of claim 1, wherein the helmet includes a securing band extending between the first side of the helmet and the second side of the helmet, wherein the securing band includes an adjustment strap located on the first side of the helmet, the second side of the helmet, or both.

9. The personal protection and ventilation system of claim 1, wherein a light source is attached to the front portion of helmet.

10. The personal protection and ventilation system of claim 9, wherein the light source is contained within a support mounted to the first portion of the helmet, further wherein the support includes a lever to adjust an area of illumination of the light source.

11. The personal protection and ventilation system of claim 1, wherein the elastic film includes a core layer disposed between a first skin layer and a second skin layer, wherein the core layer comprises polypropylene and the first skin layer and the second skin layer each comprise a copolymer of polypropylene and polyethylene.

12. The personal protection and ventilation system of any of claim 1, wherein the elastic film has a basis weight ranging from 5 gsm to 50 gsm.

13. The personal protection and ventilation system of claim 11, wherein the core layer includes a fluorochemical additive present in an amount ranging from 0.1 wt. % to 5 wt. % based on the total weight of the core layer.

14. The personal protection and ventilation system of claim 11, wherein the core layer includes a filler that is present in the core layer in an amount ranging from 50 wt. % to 85 wt. % based on the weight of the core layer.

15. The personal protection and ventilation system of claim 1, wherein the outer spunbond layer and the SMS laminate include a semi-crystalline polyolefin, wherein the semi-crystalline polyolefin includes a copolymer of propylene and ethylene, wherein the ethylene is present in an amount ranging from 1 wt. % to 20 wt. %.

16. The personal protection and ventilation system of claim 1, wherein the outer spunbond layer has a basis weight ranging from 5 gsm to 50 gsm and the SMS laminate has a basis weight ranging from 10 gsm to 60 gsm.

17. The personal protection and ventilation system of claim 1, wherein the outer spunbond layer and the SMS laminate each include a slip additive, wherein the slip additive comprises erucamide, oleamide, stearamide, behenamide, oleyl palmitamide, stearyl erucamide, ethylene bis-oleamide, N,N'-Ethylene Bis(Stearamide) (EBS), or a combination thereof, wherein the slip additive is present in the outer spunbond layer in an amount ranging from 0.1 wt. % to 4 wt. % based on the total weight of the outer spunbond layer, and wherein the slip additive is present in a layer of the SMS laminate in an amount ranging from 0.25 wt. % to 6 wt. % based on the total weight of the layer.

18. The personal protection and ventilation system of claim 1, wherein the rear panel comprises a SMS laminate.

19. The personal protection and ventilation system of claim 18, wherein the rear panel has a basis weight ranging from 20 gsm to 80 gsm.

20. The personal protection and ventilation system of claim 1, wherein the rear panel includes a slip additive comprising erucamide, oleamide, stearamide, behenamide, oleyl palmitamide, stearyl erucamide, ethylene bis-oleamide, N,N'-Ethylene Bis(Stearamide) (EBS), or a combination thereof, wherein the slip additive is present in the rear panel in an amount ranging from 0.25 wt. % to 6 wt. % based on the total weight of each spunbond layer in the SMS laminate of the rear panel.

* * * * *